United States Patent
Ohura

(10) Patent No.: US 10,222,348 B2
(45) Date of Patent: Mar. 5, 2019

(54) NANOPORE-BASED ANALYSIS DEVICE

(75) Inventor: Takeshi Ohura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 263 days.

(21) Appl. No.: 14/237,176

(22) PCT Filed: Jul. 25, 2012

(86) PCT No.: PCT/JP2012/068765
§ 371 (c)(1),
(2), (4) Date: Feb. 5, 2014

(87) PCT Pub. No.: WO2013/021815
PCT Pub. Date: Feb. 14, 2013

(65) Prior Publication Data
US 2014/0158540 A1     Jun. 12, 2014

(30) Foreign Application Priority Data
Aug. 9, 2011  (JP) ................................. 2011-173567

(51) Int. Cl.
G01N 27/447       (2006.01)
G01N 33/487       (2006.01)

(52) U.S. Cl.
CPC .  G01N 27/44791 (2013.01); G01N 33/48721 (2013.01); G01N 33/48728 (2013.01)

(58) Field of Classification Search
CPC ....... G01N 33/48721; G01N 33/48728; G01N 33/44791; C12Q 1/6869; B82Y 5/00
See application file for complete search history.

(56) References Cited

U.S. PATENT DOCUMENTS 6,627,067 B1 *  9/2003  Branton ................ B24B 37/013
                                                  204/403.06
2004/0144658 A1 *  7/2004  Flory .................... B82Y 10/00
                                                      205/777.5
(Continued)

FOREIGN PATENT DOCUMENTS

CN       102095768 A  *  6/2011
CN       102095768 A  *  6/2011 ............. B82Y 15/00
(Continued)

OTHER PUBLICATIONS

Japanese Office Action received in corresponding Japanese Application No. 2011-173567 dated Sep. 16, 2014.
(Continued)

*Primary Examiner* — Maris R Kessel
(74) *Attorney, Agent, or Firm* — Mattingly & Malur, PC

(57) ABSTRACT

The biological polymer analyzing equipment with nanopore includes a chamber part having a chamber having a sample introduction section and a sample outflow section separated by a substrate; a first electrode provided in the sample introduction section and a second electrode provided in the sample outflow section; a thin membrane formed on the substrate; a nanopore provided in the thin membrane of the substrate and communicating between the sample introduction section and the sample outflow section; a third electrode provided near the nanopore of the substrate; and a voltage applying member to electrodes, wherein the voltage applying member includes a member for applying voltages between the first electrode and the third electrode, between the first electrode and the second electrode, respectively, and between the third electrode and the second electrode, and relates to a method for analyzing a biological polymer using the biological polymer analyzing equipment with nanopore.

14 Claims, 18 Drawing Sheets

(56) References Cited

U.S. PATENT DOCUMENTS

| | | |
|---|---|---|
| 2004/0149580 A1 | 8/2004 | Flory |
| 2005/0202444 A1 | 9/2005 | Zhu |
| 2006/0073489 A1 | 4/2006 | Li et al. |
| 2007/0138132 A1* | 6/2007 | Barth .................. B82Y 5/00 216/56 |
| 2008/0171316 A1* | 7/2008 | Golovchenko et al. .......... 435/6 |
| 2008/0187915 A1 | 8/2008 | Polonsky et al. |
| 2008/0248561 A1 | 10/2008 | Golovchenko et al. |
| 2008/0257859 A1 | 10/2008 | Golovchenko et al. |
| 2009/0136958 A1 | 5/2009 | Gershow et al. |
| 2010/0327847 A1* | 12/2010 | Leiber ................ B82Y 15/00 324/71.1 |
| 2012/0132893 A1* | 5/2012 | Heo .................. H01L 29/0657 257/29 |
| 2012/0193236 A1* | 8/2012 | Peng ............... G01N 33/48721 204/603 |
| 2013/0037410 A1* | 2/2013 | Xu ..................... B82Y 15/00 204/601 |

FOREIGN PATENT DOCUMENTS

| | | |
|---|---|---|
| JP | 2004-233353 A | 8/2004 |
| JP | 2004-233356 A | 8/2004 |
| JP | 2005-257687 A | 9/2005 |
| JP | 2006-113057 A | 4/2006 |
| JP | 2008-536124 A | 9/2008 |
| JP | 2010-230614 A | 10/2010 |
| JP | 2011-501806 A | 1/2011 |
| WO | 2010/117470 A2 | 10/2010 |

OTHER PUBLICATIONS

Kasianowicz et al., "Characterization of individual polynucleotide molecules using a membrane channel", Proc. Natl. Acad. Sci. U.S.A., Nov. 1996, vol. 93, pp. 13770-13773.

Li et al., "Ion-beam sculpting at nanometre length scales", Nature, Jul. 2001, vol. 412, pp. 166-169.

Storm et al., "Fabrication of solid-state nanopores with single-nanometre precision", Nature Materials, Aug. 2003, vol. 2, pp. 537-540.

Fologea et al., "Detecting Single Stranded DNA with a Solid State Nanopore", Nano Letters, 2005, vol. 5, No. 10, pp. 1905-1909.

Zwolak et al., "Electronic Signature of DNA Nucleotides via Transverse Transport", Nano Letters, 2005, vol. 5, No. 3, pp. 421-424.

Taniguchi et al., "Fabrication of the gating nanopore device", Applied Physics Letters, 2009, vol. 95, pp. 123701-1 to 123701-3.

Sigalov et al., "Detection of DNA Sequences Using an Alternating Electric Field in a Nanopore Capacitor", Nano Letters, 2008, vol. 8, No. 1, pp. 56-63.

Wanunu et al., "Electrostatic focusing of unlabelled DNA into nanoscale pores using a salt gradient", Nature Nanotechnology, 2009, vol. 5.

European Search Report for EP12822028 dated Feb. 27, 2015.

* cited by examiner

Fig. 3-1
(a) Plane view
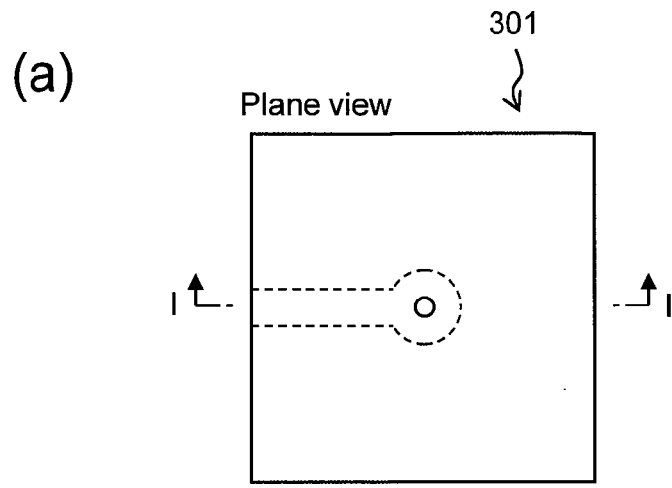
(b) A-A line cross-sectional view
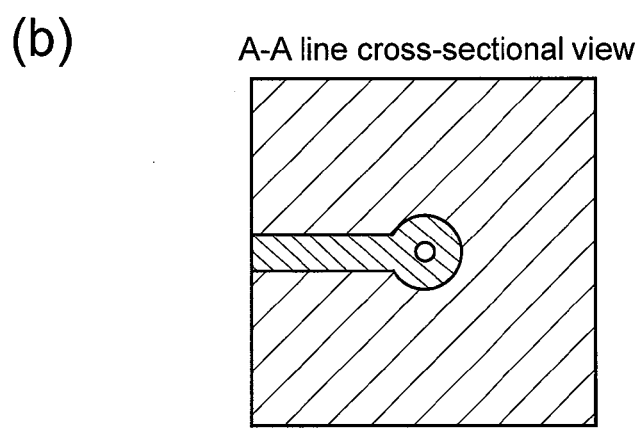
(c) I-I line cross-sectional view
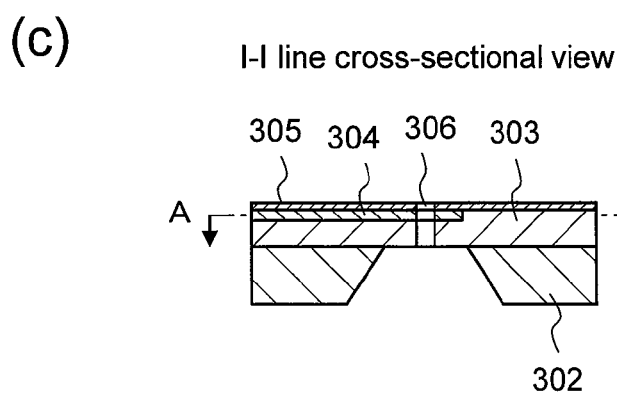

Fig. 3-2
(a)
Plane view 307
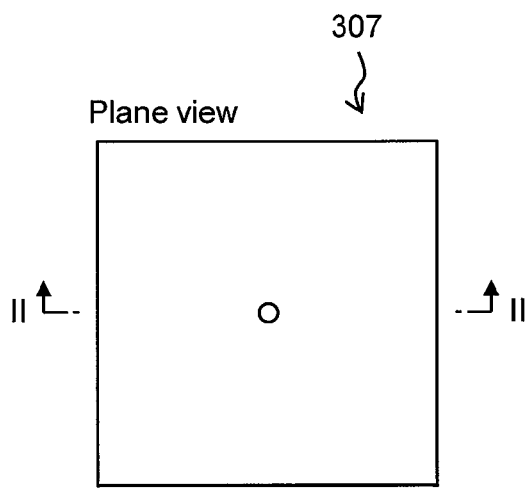
(b)
B-B line cross-sectional view
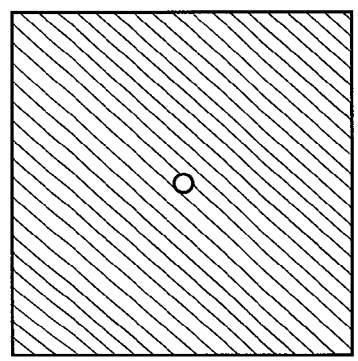
(c)
II-II line cross-sectional view
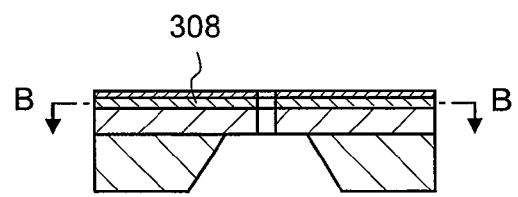

(a)

Plane view　309

(b)

C-C line cross-sectional view (c)

III-III line cross-sectional view 312　310　311

Fig. 3-4
(a)
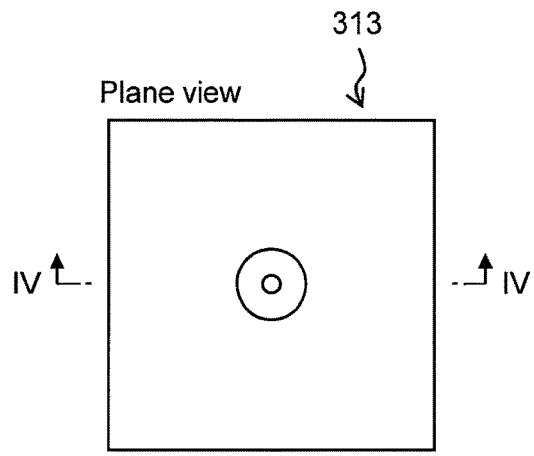
Plane view
(b)
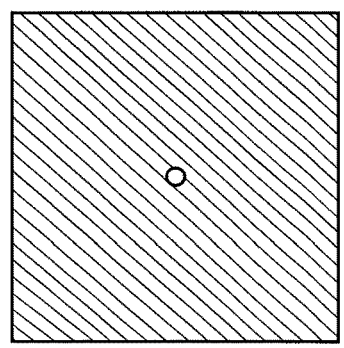
D-D line cross-sectional view
(c)
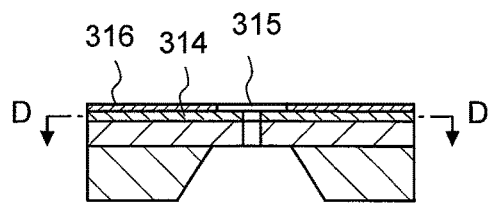
IV-IV line cross-sectional view (a) 
Plane view — 317

(b) 
E-E line cross-sectional view (c) 
V-V line cross-sectional view 322  320  318  319

321

Fig. 3-6
(a)
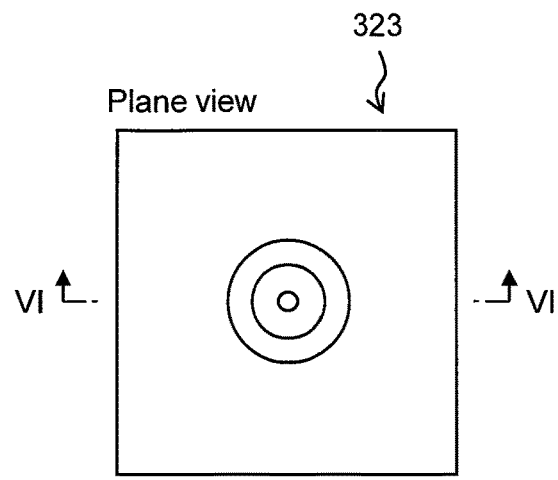
(b)
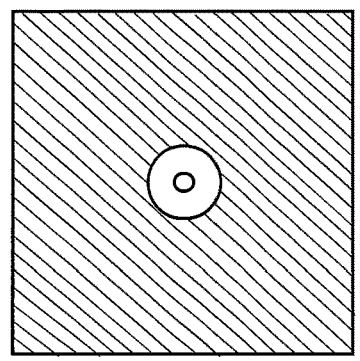
(c)
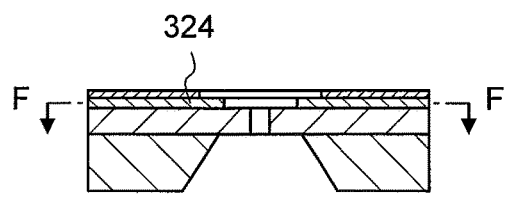

Fig. 3-7
(a)
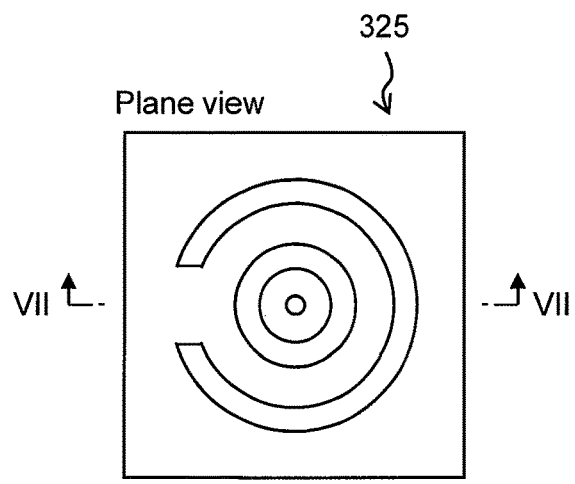
(b)
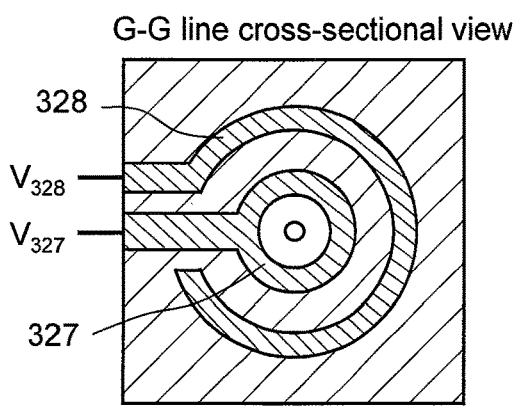
(c)
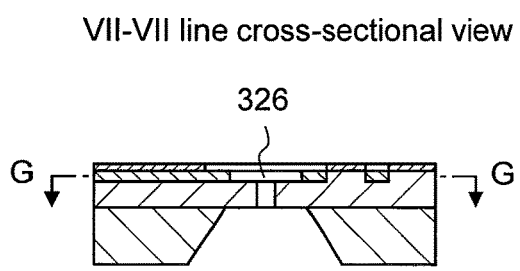

Fig. 3-8
(a)
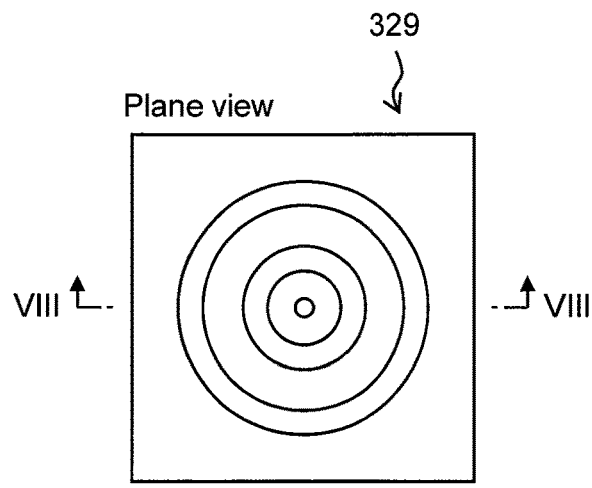
(b)
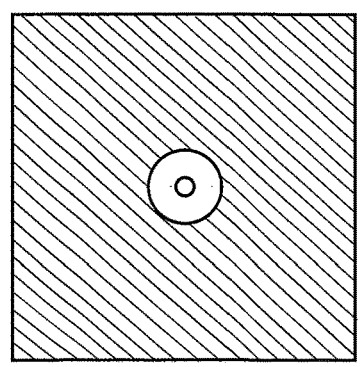
(c)
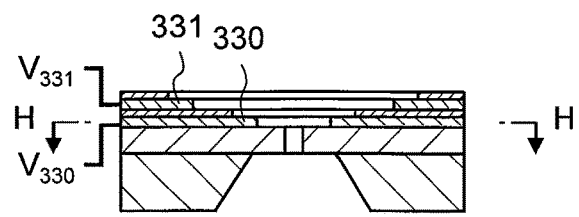

(a)

(b)

(a)

(b)

(a)

(b)

(a)

(b)

(a)

(b)

(a)

(b)

NANOPORE-BASED ANALYSIS DEVICE

TECHNICAL FIELD

The present invention relates to an equipment for analyzing a biological polymer such as a DNA and a protein via transferring the biological polymer through a nanometer-sized pore (referred to as nanopore in the present application). The present invention relates in particular to a nanopore-based analysis equipment capable of improving transfer frequency of a biological polymer through a nanopore.

BACKGROUND ART

Development of methods for analyzing a high molecular polymer such as a DNA and a protein using a nanometer-sized pore called as a nanopore has been advanced. It has been technically difficult to open the nanopore, however it has been realized to open the nanopore for the first time in a biological field by introducing an ion channel to a lipid bilayer membrane (Non Patent Literature 1). Moreover, a measurement method according to a patch-clamp method used in an ion channel measurement in a living body has been also developed as a measurement method using the nanopore. Next, opening the nanopore by utilizing a semiconductor process has been tried, and a method by an ion beam (Non Patent Literature 2) and a method by an electron beam (Non Patent Literature 3) have been developed.

As the nanopore can be created, the methods for analyzing a polymer molecule such as a DNA and a protein have been developed. Principal methods necessary for analysis with nanopore are the following two methods.

1. Detection method: those for detecting a physical change of a polymer molecule while the polymer molecule is transferred through the nanopore
2. Polymer driving method: those for transferring a polymer molecule to make the polymer molecule pass through the nanopore As the detection method, a current blockade method, a tunneling current method, and a capacitance measurement method are known. The current blockade method is a method of detecting blocking effect caused by partially blocking a nanopore opening with a polymer molecule (Non Patent Literature 4). A specific structure is a structure obtained by separating a space into two by a membrane having a nanopore, filling each space with a liquid containing an ion, and disposing an electrode in each space. When a given voltage is applied to the electrodes, the ion is driven through the nanopore and thus a current flows (ionic current). When a charged polymer molecule is present, the polymer molecule is also attracted to one side and transferred through the nanopore by an electric potential difference. Since the nanopore opening is partially blocked at the time of the transfer, the ion becomes hard to flow through the nanopore and the amount of ionic current is lowered. The current blockade method is a method of analyzing the presence of a polymer molecule or a component of a polymer molecule by detecting the lowering of the electric current value. The extent of the resistance to flow of an ion is affected by the charged state of the polymer molecule and the interaction with a nanopore wall in addition to the area of the nanopore opening.

On the other hand, the tunneling current method is a method of analyzing the presence of a polymer molecule or a component of a polymer molecule by detecting a tunneling current flowing through a slight gap between an electrode for a tunneling current provided near the nanopore and the polymer molecule when the polymer molecule is transferred through the nanopore (Non Patent Literature 5 and Non Patent Literature 6).

The capacitance measurement method is a method of analyzing the presence of a polymer molecule or a component of a polymer molecule by detecting the change in the capacitance of a nanopore-having membrane caused by the partial blockage of nanopore during the transfer of the polymer molecule through the nanopore (Non Patent Literature 7).

Moreover, the polymer driving method includes a differential voltage driven method, an enzymatic driven method, and a force driven method. The differential voltage driven method is a method of transferring a charged polymer molecule according to an electric field gradient by disposing electrodes to two spaces separated by a membrane having a nanopore and applying voltages to the electrodes as described for the current blockade method. Examples of its advantages include that the differential voltage driven method can be realized by a simple structure and unnecessary load is not posed to the polymer molecule.

The enzymatic driven method is a method of transferring a polymer molecule by disposing an enzyme near the nanopore and utilizing the reaction of the polymer molecule with the enzyme. For example, there is a method of transferring a DNA nucleotide by nucleotide by disposing a DNA polymerase near the nanopore and causing to synthesize a double strand DNA in the case where the polymer molecule is a single strand DNA. It is necessary that the DNA be located near the DNA polymerase in the enzymatic driven method, and therefore it is preferred to collect the DNA near the nanopore using the differential voltage driven method in combination in view of improving efficiency.

The force driven method is a method of realizing the transfer of a polymer molecule by fixing the polymer molecule to a bead and transferring the bead by optical tweezers. It is necessary that an end of the polymer molecule where the bead is not attached be inserted in the nanopore in the force driven method, and the differential voltage driven method is adopted for the insertion.

Accordingly, the differential voltage driven method is used, as one providing a driving force to carry the sample to the nanopore opening, in combination with any of the methods.

The sample is carried to the nanopore opening via the following three transferring states and is transferred through the nanopore. The first is the transfer by diffusion, the second is the transfer by electrophoresis, and the third is the probability of accession of an end of a polymer molecule to the nanopore opening when the sample is a long chain (Non Patent Literature 8). The electric potential difference largely affects in the second and the third transfer states.

In the conventional analysis with nanopore, since the frequency of accession of a sample to the nanopore opening is lowered when the sample has a low concentration, the transfer frequency through the nanopore is also lowered, thereby causing a a problem that the throughput in the measurement is lowered.

CITATION LIST

Non Patent Literature

Non Patent Literature 1: Kasianowicz J. J.; Brandin E.; Branton D.; Deamer D. W.: Proc. Natl. Acad. Sci. U.S.A. 1996, 93, 13770-13773

Non Patent Literature 2: Li J.; D. Stein; C. McMullan; D. Branton; M. J. Aziz; J. A. Golovchenko J. A.: 2001, Nature, 412, 166

Non Patent Literature 3: Storm A. J.; J. H. Chen; X. S. Ling; H. Zandbergen; C. Dekker: 2003, Nat. Mater. 2, 537540

Non Patent Literature 4: D. Fologea; M. Gershow; B. Ledden; D. S. McNabb; J. A. Golvchenko; J. Li: Nano Lett 2005, 5, 10, 1905.

Non Patent Literature 5: M. Zwolak; M. D. Ventra: Nano Lett 2005, 5, 3, 421

Non Patent Literature 6: M. Taniguchi; M. Tsutsui; K. Yokota; T. Kawai: Appl Phys Lett 95, 123701 (2009)

Non Patent Literature 7: G. Sigalov; J. Corner; G. Timp; A. Aksimentiev: Nano Lett 2008, 8, 1, 56.

Non Patent Literature 8: M. Wanunu; W. Morrison; Y. Rabin; A. Y. Grosberg; A. Meller: Nat. Nano. 5, 160, 2009

SUMMARY OF INVENTION

Technical Problem

The object of the present invention is to provide a biological polymer analyzing equipment with nanopore capable of, in a measurement method using a nanopore, improving transfer frequency through the nanopore with regard to a low concentration sample to improve the throughput and a method for analyzing a biological polymer using the biological polymer analyzing equipment with nanopore.

Solution to Problem

The present inventors have made diligent studies to solve the problem to succeed in expanding an electric potential difference near the nanopore opening on the side where a sample is introduced by applying voltage to an electrode provided near the nanopore and have completed the present invention, thereby collecting the biological polymer in the sample at the nanopore opening and transferring the biological polymer through the nanopore efficiently.

Namely, the present invention includes the following.

[1] A biological polymer analyzing equipment with nanopore comprising a chamber part comprising:

a chamber having a sample introduction section and a sample outflow section separated by a substrate;

a first electrode provided in the sample introduction section and a second electrode provided in the sample outflow section;

a thin membrane formed on the substrate;

a nanopore provided in the thin membrane of the substrate and communicating between the sample introduction section and the sample outflow section;

a third electrode provided near the nanopore of the substrate; and a voltage applying member, wherein the voltage applying member comprises a member for applying voltages between the first electrode and the third electrode, between the first electrode and the second electrode, and between the third electrode and the second electrode.

[2] The biological polymer analyzing equipment with nanopore according to [1], wherein the substrate further comprises a measuring electrode provided facing the nanopore.

[3] The biological polymer analyzing equipment with nanopore according to [1] or [2], wherein the nanopore has a diameter of 1 to 100 nm at the minimum diameter part.

[4] The biological polymer analyzing equipment with nanopore according to [1] to [3], wherein the voltage applying member is configured to reversibly switch an electric potential difference between the third electrode and the second electrode.

[5] The biological polymer analyzing equipment with nanopore according to [2], wherein at least a pair of the measuring electrodes are disposed facing each other with the nanopore sandwiched therebetween.

[6] The biological polymer analyzing equipment with nanopore according to [2], comprising a measuring electrode disposed facing the third electrode with the nanopore sandwiched therebetween.

[7] The biological polymer analyzing equipment with nanopore according to [2], wherein at least a pair of the measuring electrodes are disposed in parallel along an axis direction of the nanopore.

[8] The biological polymer analyzing equipment with nanopore according to [2], wherein the third electrode and the measuring electrode are disposed in parallel along an axis direction of the nanopore and the measuring electrode is provided at a position on a side closer to the sample outflow section than the third electrode.

[9] The biological polymer analyzing equipment with nanopore according to [1] to [8], wherein the third electrode is provided near a nanopore opening on the sample introduction section side.

[10] The biological polymer analyzing equipment with nanopore according to [2] to [5] and [7] to [9], wherein the measuring electrode is provided near a nanopore opening or in the thin membrane.

[11] The biological polymer analyzing equipment with nanopore according to [1] to [10], wherein the third electrode covers a whole surface of the thin membrane except for a nanopore opening.

[12] The biological polymer analyzing equipment with nanopore according to [1] to [10], wherein the third electrode is provided around a nanopore opening or the third electrodes are disposed at positions facing each other with the nanopore between the third electrodes.

[13] The biological polymer analyzing equipment with nanopore according to any one of [1] to [12], wherein the third electrode comprises two or more electrodes disposed in a multiple array and/or a multilayer.

[14] The biological polymer analyzing equipment with nanopore according to [1] to [13], comprising a plurality of the chamber parts.

[15] A method for analyzing a biological polymer comprising: introducing a sample solution comprising the biological polymer to the sample introduction section of the biological polymer analyzing equipment with nanopore according to [1] to [14]; applying voltage between the third electrode and the first electrode to collect a charged biological polymer; transferring the charged biological polymer through the nanopore; and measuring the biological polymer while transferred through a nanopore.

[16] The method according to [15], comprising applying voltages to the first, the second, and the third electrodes so that an electric potential of the third electrode becomes higher than an electric potential of the first electrode and equal to or lower than an electric potential of the second electrode, to collect a negatively charged biological polymer.

[17] The method according to [15], comprising applying voltages to the first, the second, and the third electrodes so that an electric potential of the third electrode becomes higher than an electric potential of the first electrode and equal to or higher than an electric potential of the second electrode and thereafter changing the voltages so that the electric potential of the third electrode becomes lower than the electric potential of the second electrode, to collect a negatively charged biological polymer and facilitate the transfer of the negatively charged biological polymer through the nanopore.

[18] The method according to [15], comprising applying voltages to the first, the second, and the third electrodes so that an electric potential of the third electrode becomes lower than an electric potential of the first electrode and equal to or higher than an electric potential of the second electrode, to collect a positively charged biological polymer.

[19] The method according to [15], comprising applying voltages to the first, the second, and the third electrodes so that an electric potential of the third electrode becomes lower than an electric potential of the first electrode and equal to or lower than an electric potential of the second electrode and thereafter changing the voltages so that the electric potential of the third electrode becomes higher than the electric potential of the second electrode, to collect a positively charged biological polymer and facilitate the transfer of the positively charged biological polymer through the nanopore.

[20] The method according to [15] to [19], wherein the biological polymer is selected from the group consisting of a nucleic acid, a peptide nucleic acid, a protein, a polypeptide, and a carbohydrate molecule.

The present description includes the disclosure in Japanese Patent Application No. 2011-173567 to which the present application claims a priority.

Advantageous Effects of Invention

According to the present invention, the transfer frequency of a biological polymer through nanopore can be increased and the throughput in a measurement method with nanopore can be improved.

BRIEF DESCRIPTION OF THE DRAWINGS

FIG. 3-1 is a schematic diagram of a nanopore substrate on which an electrode is provided near a nanopore.

FIG. 3-2 is a schematic diagram of a nanopore substrate on which an electrode is provided to cover a whole surface thereof.

FIG. 3-3 is a schematic diagram of a nanopore substrate on which an electrode is provided around a nanopore.

FIG. 3-4 is a schematic diagram of a nanopore substrate on which an electrode is provided to cover a whole surface around a nanopore.

FIG. 3-5 is a schematic diagram of a nanopore substrate on which an electrode is provided in a position around a nanopore but retreated from an end of the nanopore.

FIG. 3-6 is a schematic diagram of a nanopore substrate on which an electrode is provided to cover a whole surface around a nanopore except for a retreating region from an end of a nanopore.

FIG. 3-7 is a schematic diagram of a nanopore substrate on which electrodes are provided in positions around a nanopore but retreated from an end of the nanopore in a multiple array.

FIG. 3-8 is a schematic diagram of a nanopore substrate on which electrodes are provided in positions around a nanopore but retreated from an end of the nanopore in a multiple array and in a multilayer.

FIG. 4 is a schematic diagram of an analysis chamber part comprising a nanopore substrate having a tunneling current measuring electrode and a sample collecting electrode disposed thereon facing each other with a nanopore sandwiched therebetween.

FIG. 5 is a schematic diagram of an analysis chamber part comprising a nanopore substrate on which tunneling current measuring electrodes disposed facing each other with a nanopore sandwiched therebetween also work as sample collecting electrodes.

FIG. 6 is a schematic diagram of an analysis chamber part comprising a nanopore substrate having a tunneling current measuring electrode and a sample collecting electrode disposed in parallel along an axis direction of a nanopore.

FIG. 7 is a schematic diagram of an analysis chamber part comprising a nanopore substrate on which one of tunneling current measuring electrodes disposed in parallel along an axis direction of a nanopore also works as a sample collecting electrode.

FIG. 8 is a schematic diagram of an analysis chamber part comprising a nanopore substrate having a capacitance measuring electrode and a sample collecting electrode disposed in parallel along an axis direction of a nanopore.

FIG. 11-1 is a schematic diagram of an analysis chamber part comprising a nanopore substrate having a sample collecting electrode near a biological nanopore.

FIG. 11-2 is a schematic diagram of an analysis chamber part comprising a nanopore substrate having a biological nanopore directly provided at a hole of a solid membrane (thin membrane) and a sample collecting electrode near the nanopore.

DESCRIPTION OF EMBODIMENTS

Figure 1:
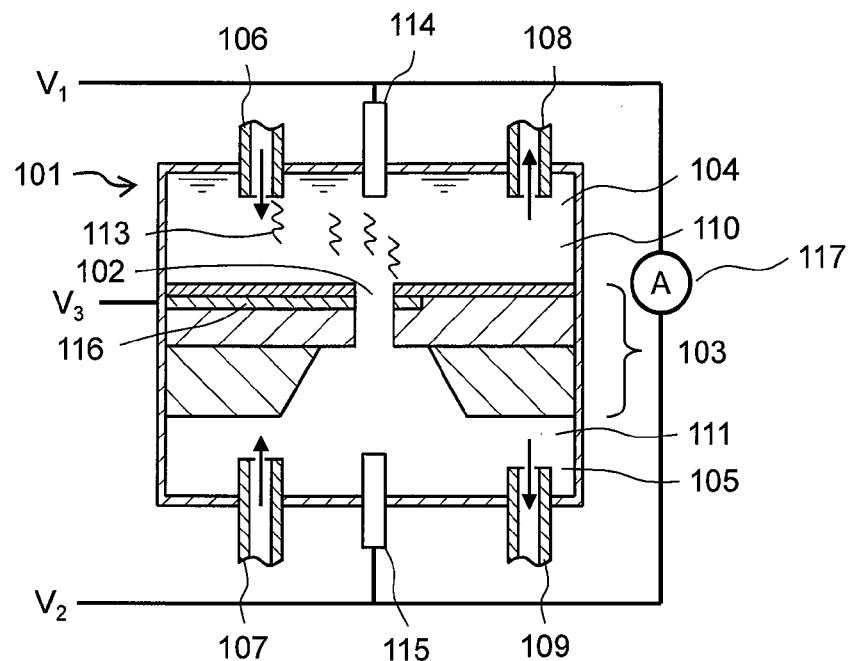
FIG. 1 is a schematic diagram of an analysis chamber part of an analyzing equipment with nanopore comprising a nanopore substrate on which a third electrode for collecting a sample at a nanopore opening is provided.

Hereinafter, the present invention will be described in detail.

The present invention relates to a biological polymer analyzing equipment with nanopore wherein voltage is applied to an electrode provided near the nanopore to increase an electric potential difference near the nanopore, thereby collecting a biological polymer near a nanopore and transferring the biological polymer through the nanopore with high frequency, and a method for analyzing a biological polymer using the biological polymer analyzing equipment with nanopore.

The biological polymer analyzing equipment with nanopore according to the present invention has a chamber part and a substrate provided in the chamber part. The substrate has a base (base material), a thin membrane formed facing the substrate, a nanopore provided in the thin membrane and communicating between a sample introduction section and a sample outflow section, a sample collecting electrode provided near the nanopore (also referred to as third electrode in the present description), and so on, and is provided between the sample introduction section and the sample outflow section in the chamber. The substrate may have an insulating layer provided facing the sample collecting electrode (third electrode). Preferably, the substrate is a solid substrate.

In the present invention, the substrate, except for an electrode, can be made from an electrical insulator material such as an inorganic material and an organic material (including a polymer material). Examples of the electrical insulator material that constitutes the substrate include silicon, silicon compounds, glass, quartz, polydimethylsiloxanes (PDMS), polytetrafluoroethylenes (PTFE), polystyrenes, polypropylenes. Examples of the silicon compounds include silicon nitride, silicon oxide, silicon carbide, silicon oxynitride. Particularly, the base (base material) that constitutes a support part of the substrate can be prepared by any of these materials, but the base material may be silicon or a silicon compound for example.

The size and the thickness of the substrate are not particularly limited as long as the nanopore can be provided. The substrate can be prepared by a known method in the technical field or is available as a commercial product. For example, the substrate can be prepared using techniques such as a photolithography or electron beam lithography, an etching, a laser ablation, an injection molding, a casting, a molecular beam epitaxy, a chemical vapor deposition (CVD), and an electron beam or focused ion beam methods. Coating may be applied to the substrate for the purpose of avoiding the adsorption on the surface by other molecules.

The thickness of the substrate is preferably 100 μm to 1000 μm. The substrate has at least one nanopore. The nanopore is specifically provided in the thin membrane but may be optionally provided together in the base (base material), the electrode, and the insulator. The "nanopore" and the "pore" according to the present invention mean a pore that is nanometer (nm)-sized (namely, a diameter of 1 nm or more and less than 1 μm), penetrates the substrate, and communicates between the sample introduction section and the sample outflow section.

Preferably, the substrate has a thin membrane for providing the nanopore. Namely, the thin membrane is formed on the substrate, of which the material and the thickness is suitable for forming a nano-sized pore, which enables easily and efficiently providing a nanopore on the substrate. It is preferable that the material of the thin membrane is, for example, silicon oxide ($SiO_2$), silicon nitride (SiN), silicon oxynitride (SiON), a metal oxide, or a metal silicate, from the standpoint of forming the nanopore. Moreover, the thin membrane (and optionally, the whole substrate) may be substantially transparent. Here, "substantially transparent" means that external light can be transmitted by about 50% or more, preferably 80% or more. Moreover, the thin membrane may be a monolayered or a multilayered. The thickness of the thin membrane is 1 nm to 200 nm, preferably 1 nm to 50 nm, more preferably 1 nm to 20 nm. The thin membrane can be formed on the substrate by a known method in the technical field, for example, by low pressure chemical vapor deposition (LPCVD).

It is preferable to provide an insulating layer on the thin membrane. The thickness of the insulating layer is preferably 5 nm to 50 nm. Any insulator material can be used for the insulating layer, but it is preferable to use, for example, silicon or a silicon compound (such as silicon nitride or silicon oxide).

The "opening" of the nanopore or the pore in the present invention means an opening circle of the nanopore or the pore at where the nanopore or the pore contacts a sample solution. During the analysis of a biological polymer, a biological polymer, an ion, or the like in a sample solution enter the nanopore from one opening of the nanopore and flows out of the nanopore from the opening on the same or opposite side of the nanopore.

As the size of the nanopore, an appropriate size of the nanopore can be selected depending on the type of the biological polymer that is a subject of analysis. The nanopore may have a uniform diameter but may have different diameters depending on the part. The nanopore may be connected to the pore having a diameter of 1 μm or more. It is preferable that the nanopore provided in the thin membrane of the substrate has a diameter at the minimum diameter part, namely the smallest diameter that the nanopore has, of 100 nm or less, 1 nm to 100 nm for example, preferably 1 nm to 50 nm, 1 nm to 10 nm for example, specifically 1 nm or more to 5 nm or less, 3 nm or more to 5 nm or less, etc. It is preferable that the measuring electrode is provided at such site of the nanopore where the diameter is 100 nm or less, preferably 10 nm or less, 1 nm to 100 nm or 1 nm to 5 nm for example, and used as a detecting part.

The diameter of a ssDNA (single strand DNA) is about 1.5 nm, and the suitable range of the diameter of the nanopore for analyzing the ssDNA is about 1.5 nm to about 10 nm, preferably about 1.5 nm to about 2.5 nm. The diameter of a ds DNA (double strand DNA) is about 2.6 nm, and the suitable range of the diameter of the nanopore for analyzing the dsDNA is about 3 nm to 10 nm, preferably 3 nm to 5 nm. Similarly in the case where another biological polymer such as, for example, a protein, a polypeptide, or a carbohydrate molecule is used as a subject of analysis, the diameter of the nanopore can be selected according to the size of the outer diameter of the biological polymer.

The depth (length) of the nanopore can be adjusted by adjusting the thickness of the substrate or the thin membrane on the substrate. It is preferable that the depth of the nanopore is set on the basis of the length of a monomer unit that constitutes the biological polymer being the subject of analysis. When selecting a nucleic acid as a biological polymer for example, it is preferable that the depth of the nanopore is set to the size of 3 nucleotides or more, for example about 1 nm or more. The shape of the nanopore (cross-sectional shape) is basically circular or approximately circular but can be made to be an elliptical shape or a polygon.

At least one nanopore can be provided in the substrate, and in the case where a plurality of the nanopores are provided, the plurality of the nanopores may be disposed regularly. The nanopore can be formed by a known method in the technical field, for example by irradiating an electron beam of a transmission electron microscope (TEM) or by using a nanolithography method or an ion beam lithography method etc.

The electrode (such as the first to the third electrodes and the measuring electrode) can be made of a metal such as a platinum group metal such as platinum, palladium, rhodium, ruthenium; gold, silver, copper, aluminum, nickel; graphite, for example graphene (may be monolayered or multilayered), tungsten, tantalum, or the like. The electrode may have any shape, however processing becomes easy by making the shape of the electrode planar.

The chamber part has a sample introduction section and a sample outflow section, a substrate, a voltage applying member, a measuring electrode for measuring a biological polymer that is passing through the nanopore, and so on. In a preferred example, the chamber part has a sample introduction section and a sample outflow section, a first electrode provided in the sample introduction section, a second electrode provided in the sample outflow section, a substrate having a third electrode, a voltage applying member to the first, the second, and the third electrode, a measuring electrode for measuring a biological polymer that is transferred through the nanopore, and so on. An ammeter may be disposed between the first electrode provided in the sample introduction section and the second electrode provided in the sample outflow section. A current between the first electrode and the second electrode may be set appropriately from the standpoint of determining the speed of the transfer of a sample through the nanopore and is preferably, but not limited to, about 100 mV to about 300 mV in the case where electrolyte liquid not containing a sample is used or in the case of a DNA for example.

In the present invention the current blockade method, the tunneling current method, the capacitance measurement method, or the like can be utilized for measuring a biological polymer that is passing through the nanopore, but not limited to these methods. A measuring electrode suitable for each measurement method is disposed suitably for use. The measuring electrode may be one, however it is preferable that one or more pairs of the measuring electrodes are used. In the case where only one measuring electrode is used, it is preferable that the measurement is carried out, for example, in combination with the third electrode although not limited thereto. The third electrode in this case works as not only a sample collecting electrode but also a measuring electrode. One or more pairs of measuring electrodes may be disposed, by every pair, facing each other with the nanopore sandwiched therebetween or in parallel along the axis direction of the nanopore. In the case where the electrodes are disposed in parallel, an insulating layer may be provided between the measuring electrodes. It is preferable that the measuring electrode is provided near the nanopore opening or in the thin membrane. In the case where the measuring electrode is not used for measurement in combination with the third electrode, it is more preferable that the measuring electrode is provided at a position on the side closer to the sample outflow section than the third electrode.

The third electrode is provided near the nanopore of the substrate. The third electrode being "provided near the nanopore" in the context of the present invention means that at least a part of the third electrode faces the nanopore or is provided at a position slightly retreated from the nanopore end (for example, at a position within 100 nm from the central axis of the nanopore opening in the vertical direction). The phrase "facing the nanopore" in the context of the present invention means that at least a part of the third electrode is in contact with the wall surface at the axis direction of the nanopore. The third electrode may cover the whole surface of the thin membrane except for the nanopore opening or may be provided around the nanopore opening. The third electrode being "provided near the nanopore" in the context of the present invention means that the third electrode is provided so as to completely surround or almost completely surround the nanopore near the nanopore (preferably 70% or more, more preferably 80% or more, for example 85% or more of the circumference of the nanopore opening). Alternatively, the third electrode may be electrodes disposed facing each other with the nanopore sandwiched therebetween. It is preferable that the third electrodes in this case are disposed in the orthogonal direction to the axis of the nanopore. The third electrode may be electrodes disposed in a multiple array. The "multiple array" in this context means that the electrodes are disposed concentrically or almost concentrically with the nanopore as a center. The third electrode may be electrodes disposed in a multilayer. Here, "multilayer" in this context means that the electrodes are disposed in layers along the axis direction of the nanopore. With regard to the multilayered electrodes, it is preferable that an insulating layer is sandwiched between the electrodes of respective layers. In addition, even in the case where the first and the second electrodes are not present, or the first and the second electrodes are not utilized for collecting a biological polymer, or the other electrodes are further present, the electrode provided near the nanopore of the substrate can be referred to as the "third electrode".

The third electrode may be optionally configured so that voltage is applied between the third electrode and another electrode that is, for example, an electrode provided at the outside of the chamber (as an example, an inflow path communicated with the sample introduction section or a sample container connected to the inflow path) and, as a result thereof, which enables the third electrode to collect a sample near the nanopore.

The biological polymer analyzing equipment with nanopore according to the present invention typically has, but not limited to, for example, an inflow and outflow path (flow path) connected to the sample introduction section and the sample outflow section, a measuring part for measuring a biological polymer that is passing through the nanopore, and so on in addition to the chamber part. The measuring part may have an amplifier for amplifying an electric signal between electrodes, an analog-digital converter for converting an analog output from the amplifier to a digital output, recording apparatus for recording a measured data, and so on. The measuring part may also be a data logger including both of a measuring member and a measured data-recording member. When the measurement in which external light (excitation light) is irradiated to a biological polymer having entered the nanopore to excite the biological polymer and generate Raman scattering light and properties of a biological polymer is analyzed based on the spectrum of Raman scattering light is carried out, the measuring part may have a light source for irradiating external light and a detector (such as a spectroscopic detector) for detecting Raman scattering light. The light source may be, but not limited to, krypton (Kr) ion laser, neodymium (Nd) laser, argon (Ar) ion laser, YAG laser, nitrogen laser, sapphire laser, or the like for example, and it is preferable that the light source irradiates external light of a wavelength of 400 to 800 nm, preferably 500 to 600 nm. Moreover, the measuring part may have a confocal lens and an objective lens, a filter, a half mirror, a confocal pinhole, and so on, in combination with light source.

Moreover, the biological polymer analyzing equipment with nanopore according to the present invention may be connected to external equipment (for example, a computer) for analyzing the measured value acquired at the measuring part.

The voltage applying member for applying voltage to the first, the second, and the third electrodes may be a power supply part for applying voltages between the electrodes. The power supply part may have a control part controlling and switching applied voltages. The voltage applying member may include a plurality of power supplies or may have a single power supply.

The voltage applying member for applying voltage to the third electrode may be a member for applying voltage between a plurality of electrodes disposed in a multiple array.

The biological polymer analyzing equipment with nanopore of the present invention more generally comprises:

a chamber having a sample introduction section and a sample outflow section separated by a substrate, a thin membrane formed on the substrate, a nanopore provided in the thin membrane of the substrate and communicating between the sample introduction section and the sample outflow section, an electrode provided near the nanopore of the substrate, and a voltage applying member for applying voltage to the electrode, wherein a sample, preferably a biological polymer (in particular, a charged biological polymer) is collected near the nanopore by generating an electric potential difference near the nanopore by the voltage applying member.

The biological polymer analyzing equipment with nanopore of the present invention typically has a chamber part comprising:

a chamber having a sample introduction section and a sample outflow section separated by a substrate;

a first electrode provided in the sample introduction section and a second electrode provide in the sample outflow section;

a thin membrane formed on the substrate;

a nanopore provided in the thin membrane of the substrate and communicate between the sample introduction section and the sample outflow section;

a third electrode provided near the nanopore of the substrate; and a voltage applying member, wherein the voltage applying member comprises a member for applying voltages between the first electrode and the third electrode, between the first electrode and the second electrode, and between the third electrode and the second electrode.

One embodiment of the biological polymer analyzing equipment with nanopore according to the present invention comprising a nanopore substrate on which the third electrode for collecting a sample at the nanopore opening is provided schematically shown in FIG. 1.

The configuration of the nanopore substrate and the chamber part with the nanopore substrate provided therein is shown in FIG. 1. As shown in FIG. 1, the chamber 101 is composed of two closed spaces separated by the substrate 103 having a nanopore 102 (nanopore substrate), namely the sample introduction section 104 and the sample outflow section 105. The sample introduction section 104 and the sample outflow section 105 are communicated with each other by the nanopore 102. The sample introduction section 104 and the sample outflow section 105 are to be filled with liquid 110 and 111 introduced through inflow paths 106 and 107 connected to both sections respectively. The liquids 110 and 111 flow out from outflow paths 108 and 109 connected to the sample introduction section 104 and the sample outflow section 105. The inflow paths 106 and 107 may be provided facing each other with the substrate sandwiched therebetween, but are not limited thereto. The outflow paths 108 and 109 may be provided facing each other with the substrate sandwiched therebetween, but are not limited thereto.

It is preferable that the liquid 110 is a sample solution containing a sample 113 to be analyzed. The liquid 110 contains an ion that becomes a charge carrier by preferably a large amount (hereinafter, referred to as electrolyte solution 112). It is preferable that the liquid 110 contains only the electrolyte solution 112 except for the sample. An aqueous solution in which a highly-ionized electrolyte is dissolved is preferable as the electrolyte solution 112, and a solution of salts, for example, an aqueous solution of potassium chloride, can be suitably used.

It is preferable that the sample 113 is one to be charged in the electrolyte solution 112. The sample 113 is typically a biological polymer.

Electrodes 114 and 115 (the first electrode and the second electrode, respectively) disposed facing each other with the nanopore 102 sandwiched therebetween are provided in the sample introduction section 104 and the sample outflow section 105. Furthermore, an electrode 116 (the third electrode) is provided near the opening of the nanopore 102 at the side where the liquid 110 contacts the liquid 110 so as to surround the nanopore 102.

In the present embodiment, the chamber part also comprises a voltage applying member for applying voltage to the electrodes 114, 115, and 116. The voltage applying member is a voltage applying member for applying voltages between electrodes 114 and 116, between electrodes 114 and 115, and between electrodes 115 and 116.

If the sample is negatively charged, the sample 113 is attracted and collected near the nanopore 102 opening on the side of the sample introduction section 104 by applying voltages so as to be V1<V3 where the electric potentials at respective electrodes generated by applying voltages to electrodes 114, 115, and 116 are expressed as V1, V2, and V3 respectively. At this time, when the voltages are simultaneously applied so as to be V3<V2, the sample 113 is transferred through the nanopore 102 and attracted near the electrode 115 in the sample outflow section 105. In this case, when a current between electrodes 114 and 115 is measured by an ammeter 117, a current in which only an ion flows can be measured if the sample 113 is not present in the nanopore 102. However, if the sample 113 is present in the nanopore, since an amount of ion that can be transferred through the nanopore 102 is limited by the volume of the sample 113, the current decreases compared with the state where only ion flows. The analysis of the sample can be carried out by measuring the reduction amount as a blocked current by the sample 113. Namely, it is preferable that the voltage applying member of the present invention is configured to be capable of applying voltages so that electric potentials of respective electrodes become V1 (the first electrode)<V3 (the third electrode)<V2 (the second electrode).

In the case where the biological polymer analyzing equipment with nanopore having the chamber part of the present embodiment is used for the analysis of a biological polymer, it is preferable that the electric potential difference between V1 and V3 is made to be large for the purpose of making the sample 113 access the nanopore opening as fast as possible. The electric potential difference between V3 and V2 affects the rate of transfer of the sample through the nanopore and output of an electric signal, and therefore it is preferable that the electric potential difference between V3 and V2 is made to be an appropriate value according to a sampling rate of a current detecting system. An output with high accuracy can also be obtained in averaging and statistical processing by making the electric potential difference between V3 and V2 small to transfer the sample through the nanopore slowly, and carrying out a plurality of measurements of the state in which the sample 113 is present in the nanopore 102.

In the case where the sample 113 is positively charged, voltages are applied in the direction contrary to the direction in the case where the sample is negatively charged. For example, V1>V3>V2.

As another embodiment, a step of collecting the sample 113 near the nanopore 102 and a step of transferring the sample 113 through the nanopore 102 may be carried out separately. In the case, the voltages are applied so as to be V1<V3 in the step of collecting the sample 113 near the nanopore 102 in the case where the sample 113 is negatively charged. V2 at this time may be any electric potential, however V2 may be made to be V3≥V2. Next, in the step of transferring the sample 113 through the nanopore 102, the voltages are applied so as to be V1≤V3<V2, or the voltages are applied so as to be V1<V2 and V3 may be made to be open. As described here, a lot of samples can be transferred in a short time by collecting the sample 113 near the opening of the nanopore 102 once and thereafter transferring the sample 113 through the nanopore 102. Namely, it is preferable that the voltage applying member of the present invention is configured to be capable of reversibly switching voltage between the third electrode and the second electrode to be capable of applying voltages so that the electric potentials of respective electrodes become V1 (the first electrode)<V3 (the third electrode) and V3 (the third electrode)≥V2 (the second electrode) simultaneously, and of applying the voltage so as to be V1≤V3<V2 or applying voltages so as to be V1<V2 and thereafter changing them to make V3 open. Here, "reversibly" means that, for example, the voltage applied state of V3≥V2, and the voltage applied state of V3<V2 or the V3 open state, are mutually and easily switchable.

In the above method, since the timing of the start of detecting the blocked current can be controlled, the detection can be carried out only during the time when the sample is passing through the nanopore and the efficient data collection becomes possible. The data of the state that the sample is not passing through the nanopore becomes a useless data in analyzing the sample except for the case where the state of a baseline is monitored. The present measurement method in which huge data are generated in a short time can avoid such useless data collection and effectively collect the data by the technique and therefore the technique can be said as an important method.

The above method can be carried out also in the case where the sample is positively charged, and in the case, the electric potential difference between respective electrodes that is opposite to the electric potential difference in the case where the sample is negatively charged should be generated in the opposite direction to the electric potential difference in the case where the sample is negatively charged.

Figure 2:
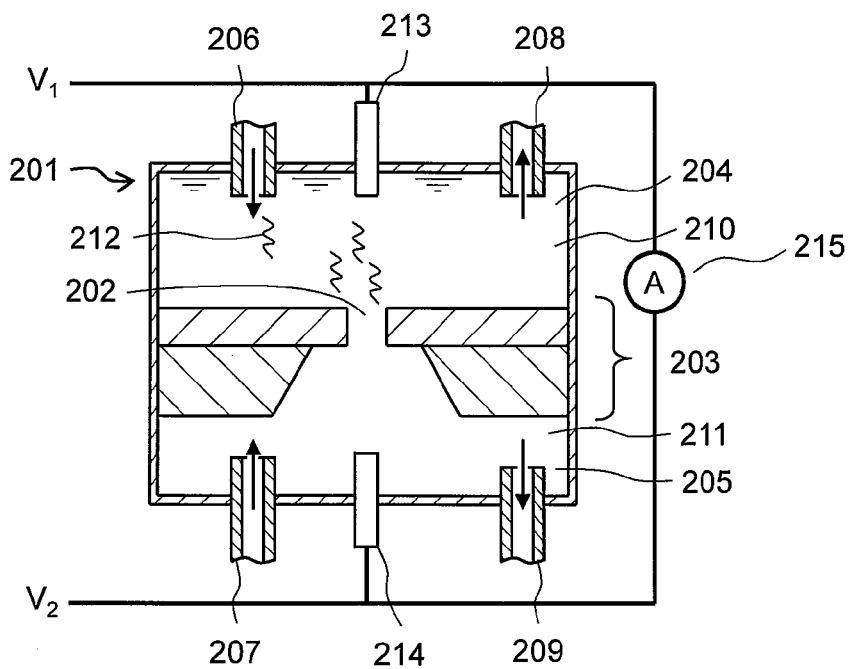
FIG. 2 is a comparison diagram of an analysis chamber part of an analyzing equipment with nanopore not having a third electrode.

The chamber part of the biological polymer analyzing equipment with nanopore according to the present invention is described in comparison to the chamber part not having the third electrode, as follows. The configuration of the chamber part in which a nanopore substrate is provided therein but the substrate does not have the third electrode is shown in FIG. 2. The chamber 201 is composed of two closed spaces 204 and 205 separated by a nanopore substrate 203 having a nanopore 202 and is filled with liquids 210 and 211 introduced through inflow paths 206 and 207 and outflow paths 208 and 209. The liquids 210 and 211 contain a large amount of ion as a charge carrier (hereinafter, referred to as electrolyte solution), furthermore either one of the liquid 210 and 211 contains a small amount of a sample 212 to be analyzed. The sample having an ion and a charge is transferred through the nanopore when voltages are applied to electrodes 213 and 214 provided on both sides of the nanopore. The electrolyte solution is similar to the above present invention, and, an aqueous solution of potassium chloride for example is used. The analysis of components of the sample 212 is carried out by the detection of the physical, electrical, and chemical interaction between the sample 212 and the nanopore 202 during the sample 212 passes through the nanopore 202. For example, when the sample 212 that is negatively charged such as a DNA is introduced in the space 204 and voltages are applied to the electrode 213 and the electrode 214 so that the electrode 214 has a higher electric potential, the amount of the ion transferring through the nanopore is reduced when the sample 212 is present in the nanopore 202 as compared with when the sample 212 is not present in the nanopore 202 and therefore the sample is analyzed by detecting (via the current blockade method) the phenomenon that the current value between the electrode 213 and the electrode 214 is reduced.

However in the case where the equipment is used and the sample 212 has a low concentration, since the frequency of accession of the sample 212 to the opening of the nanopore 202 is reduced, the frequency of detecting a signal by the transfer of the sample 212 through the nanopore 202 is also reduced and the reduction in the throughput of the measurement becomes a problem. The frequency of accession of the sample to the nanopore opening can be made to be large by making the electric potential difference large in the differential voltage driven method, however the rate at which the sample 212 is transferred through the nanopore 202 is also increased and therefore it becomes difficult to correctly acquire the signal. For example, in the case where the sample is a DNA or an RNA, it is necessary to identify each base adjacent to each other at a distance of 0.3 to 0.7 nm. Generally, when a double strand DNA of contiguous 1000 bases at a concentration of 1 nM in a 1M KCl aqueous solution are used to transfer it through a nanopore having a diameter of 5 to 10 nm and a length of 20 nm under an applied voltage of 100 mV, the frequency is 0.5 to 1 times/second and the transfer rate is 1 msec or less. Therefore a signal due to 1 base of about 100 pA has to be acquired by a high speed sampling of 1 μsec or less.

As a method for increasing the transfer frequency through nanopore, there is a method by increasing the electric potential difference near the nanopore opening by differentiating the concentrations of the KCl aqueous solutions for the liquids 210 and 211 in both sides of the nanopore 202 from each other to make a concentration gradient. However, since the saturated concentration of KCl aqueous solution is 3.4 mol/L at 20° C., there is a limit in making the concentration gradient large (M. Wanunu, W. Morrison, Y. Rabin, A. V. Grosberg, A. Meller, 2009, Nat. Nano, 379).

Improving the throughput of the measurement without changing the transfer frequency through nanopore of the sample can be realized by increasing the number of nanopores and parallelization, however it is difficult to produce a plurality of nanopores in uniform size, there is a possibility that the variation in the nanopose production results in the variation in detected signals, and therefore a detection with high accuracy is difficult.

In the case where the sample is a low concentration DNA, there is a method via amplification by a Polymerase Chain Reaction method (PCR method) or the like, however it is preferable not to use the PCR method because of a problem in terms of accuracy such as a problem that an amplification error can occur or the part where the amplification is difficult can be present or a problem that the cost becomes high by using an enzyme such as a polymerase.

On the contrary, in the biological polymer analyzing equipment with nanopore according to the present invention, the sample (a charged biological polymer) can be collected near the nanopore opening and the transfer frequency through the nanopore can be easily improved by providing the third electrode on the substrate in the chamber part and applying voltages between the electrode 114 (the first electrode) and the electrode 115 (the second electrode), and the third electrode.

Figure 3:
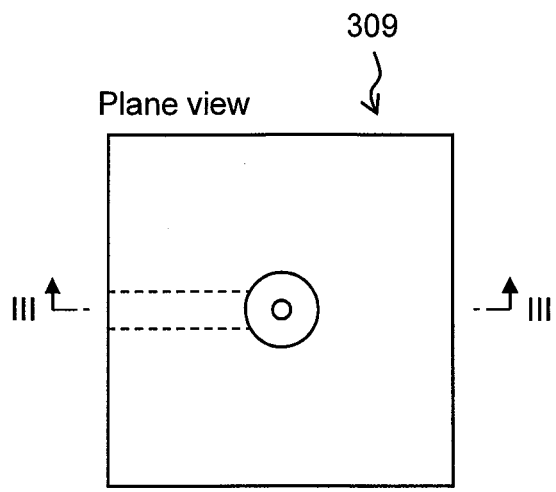
Figure 3:
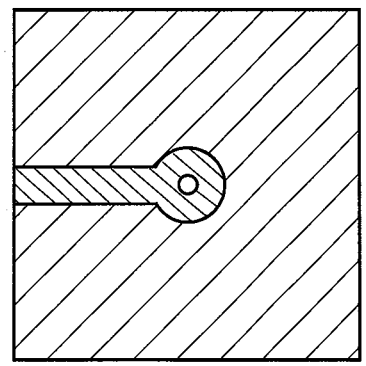
Figure 3:
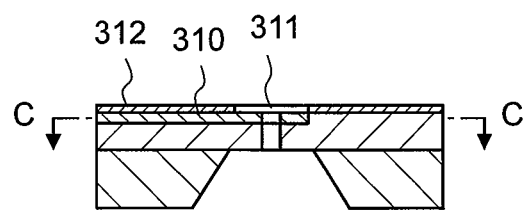
Figure 3:
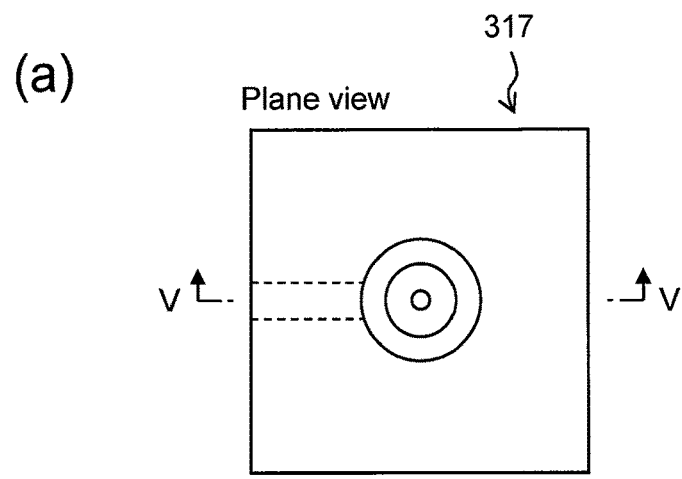

FIG. 3-1 shows one embodiment of the substrate to be used in the present invention.

FIG. 3-1 (a) shows a plane view of the substrate 301. FIG. 3-1 (b) shows a cross-sectional view taken along the line A-A of FIG. 3-1 (c). FIG. 3-1 (c) shows a cross-sectional view taken along the line I-I of FIG. 3-1 (a).

As shown in FIG. 3-1, the substrate 301 provided in the chamber is composed of a base (base material) 302, a thin membrane 303, an electrode 304, and in insulating layer 305.

A nanopore 306 that is a nanometer-sized pore is provided in the thin membrane on the substrate. The nanopore 306 penetrates the substrate.

It is preferable that the size of the nanopore 306 is 1 nm to 100 nm. The preparation of the nanopore can be carried out by a known method such as a method using a focused ion beam or a method using an electron beam (see, for example, J. Li, D. Stein et al., 2001, Nature, 412, 166, and A. J. Storm et al., 2003, Nat. Mater. 2, 537-540).

With regard to preferred examples of materials, silicon as the base 302, silicon nitride, silicon oxide, or silicon carbide as the thin membrane 303, gold, platinum, tungsten, or tantalum as the electrode 304, and silicon nitride or silicon oxide as the insulating layer 305 etc. can be advantageously used, but are not limited thereto.

It is preferable that the thickness of the substrate 301 is 100 µm to 1,000 µm. It is preferable that the thickness of the base 302 is 100 µm to 1000 µm, the thickness of the electrode 304 is 1 nm to 100 nm, and the thickness of the insulating layer is 5 nm to 50 nm. It is preferable the thickness of the thin membrane, which may change depending on the disposition and the number of the third electrodes (sample collecting electrode) and the measuring electrodes, is 1 nm to 10 nm, preferably 1 nm to 5 nm.

The electrode 304 is provided near the nanopore 306 of the substrate. The electrode 304 may be composed of a part that surrounds the nanopore 306 and a part that can work as a lead wire for applying voltage and extends from the part that surrounds the nanopore toward an outer end of the substrate. In the case, the part that surrounds the nanopore 306 and the part that can work as a lead wire respectively have a shape of a diameter of 10 nm to 1,000 nm and a width of 10 nm to 1,000 nm.

An example of a preparation procedure of the substrate having the electrode 304 and the nanopore 306 includes, but not limited to, a method comprising, for example, vapor-depositing the thin membrane 303 on the base 302, processing the electrode 304 by selective etching or lift-off process using a pattern, and vapor-depositing the insulation layer 305 thereon and thereafter processing it to make the nanopore 306. In the case of forming a plurality of nanopores, a different lead wire can be provided for each electrode surrounding each nanopore to apply a different voltage.

Moreover, FIG. 3-2 shows another embodiment 307 of the substrate.

FIG. 3-2 (a) shows a plane view of the substrate 307. FIG. 3-2 (b) shows a cross-sectional view taken along the line B-B of FIG. 3-2 (c). FIG. 3-2 (c) is a cross-sectional view taken along the line II-II of FIG. 3-2 (a).

In the embodiment shown in FIG. 3-2, the shape of the electrode (the third electrode) is different from the structure of the substrate shown in FIG. 3-1, and the electrode 308 is formed to cover the whole surface of the thin membrane on the substrate (except for the nanopore). Typically, the preparation of the electrode 308 can simply be carried out by vapor-depositing an electrode member on the whole surface of the substrate. Moreover, even in the case of forming a plurality of nanopores in the thin membrane, the same voltage can be applied to all of the nanopores at a time by the electrode 308.

FIG. 3-3 shows another embodiment 309 of the substrate.

FIG. 3-3 (a) shows a plane view of the substrate 309. FIG. 3-3 (b) shows a cross-sectional view taken along the line C-C of FIG. 3-3 (c). FIG. 3-3 (c) is a cross-sectional view taken along the line of FIG. 3-3 (a).

The embodiment shown in FIG. 3-3 is different from the structure of the substrate shown in FIG. 3-1 in the shape of the insulating layer, and the insulating layer 312 is formed so that the electrode 310 is exposed to the space 311 near the nanopore. In this case, it becomes easy to collect the sample from a wide range due to the expansion of the space capable of attracting the sample by the electrode 310 (an electric field). A method for preparing the substrate needs a processing of the insulating layer 312 by selective etching or lift-off process using a pattern.

Figure 4:
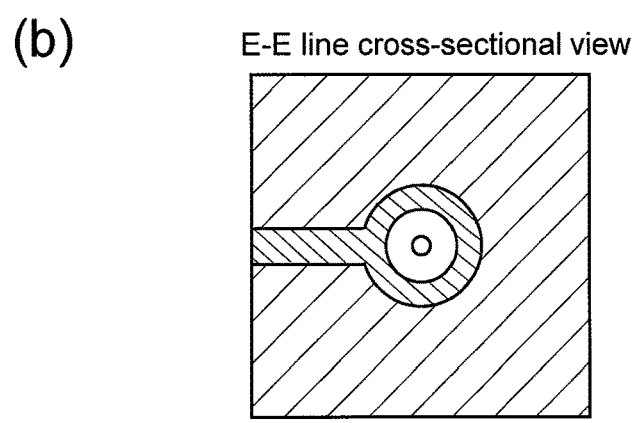

Moreover, FIG. 3-4 shows another embodiment 313 of the substrate.

FIG. 3-4 (a) shows a plane view of the substrate 313. FIG. 3-4 (b) shows a cross-sectional view taken along the line D-D of FIG. 3-4 (c). FIG. 3-4 (c) is a cross-sectional view taken along the line IV-IV of FIG. 3-4 (a).

The embodiment shown in FIG. 3-4 has a shape in which the embodiment 307 of FIG. 3-2 and the embodiment 309 of FIG. 3-3 are combined. In the embodiment, the electrode 314 is formed on the whole surface of the thin membrane, and the insulating layer 316 is formed so that the electrode 314 is exposed to the space 315. The embodiment has both of the advantages of the embodiment 307 of FIG. 3-2 and the embodiment 309 of FIG. 3-3.

Figure 5:
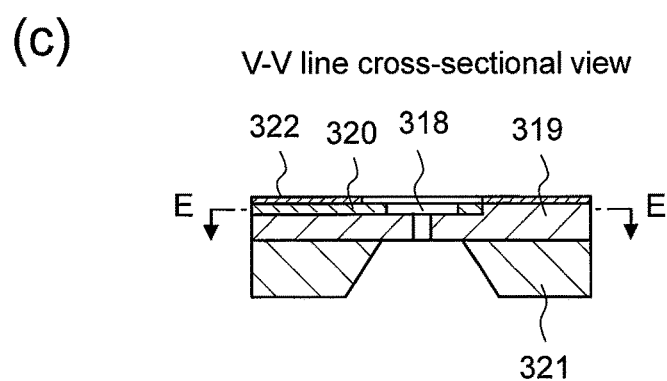
Figure 4:
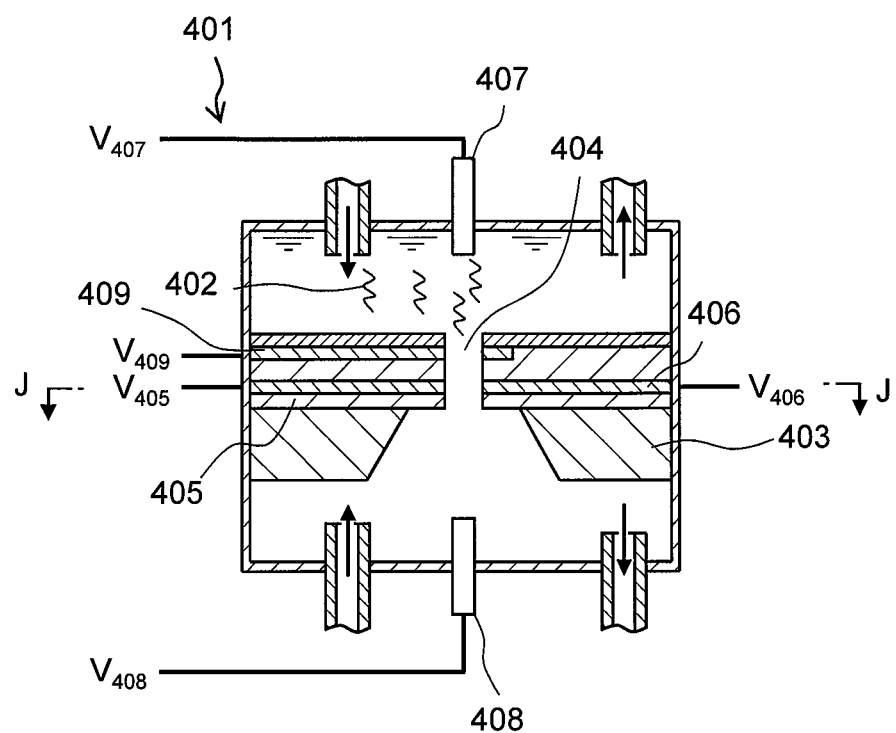
Figure 4:
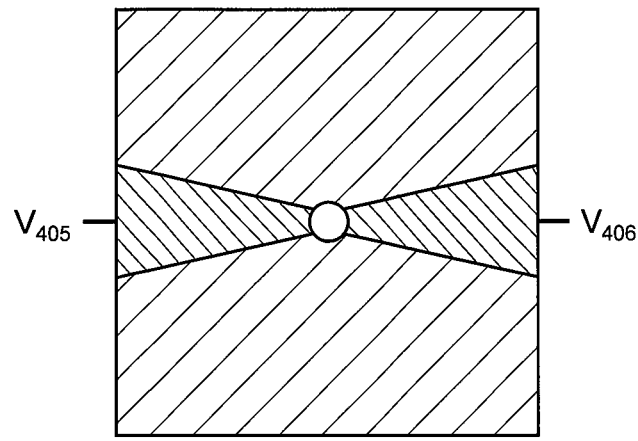
Figure 5:
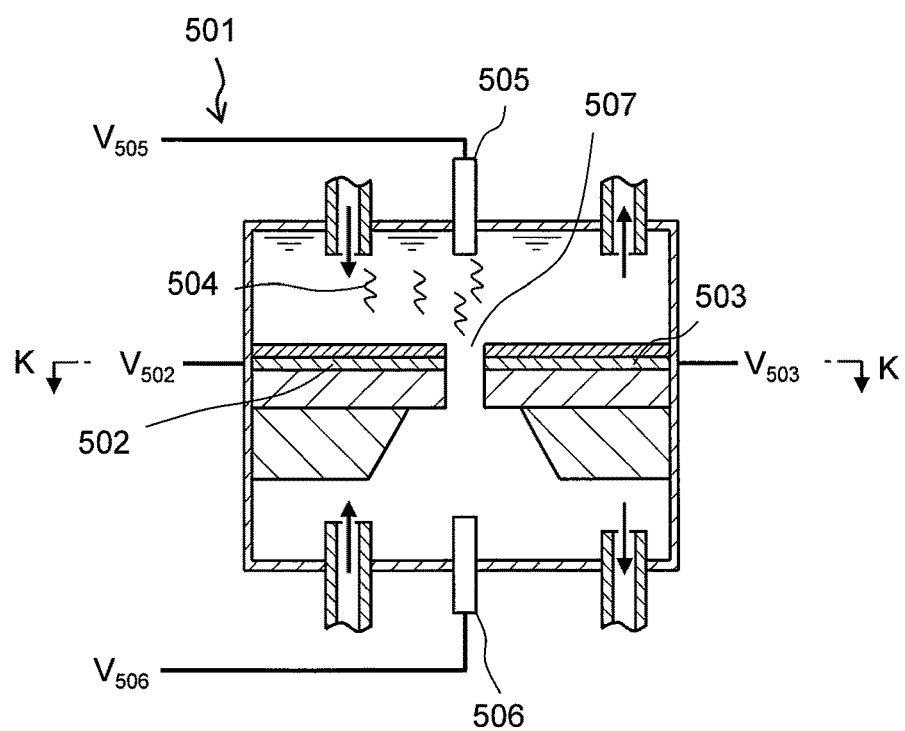
Figure 5:
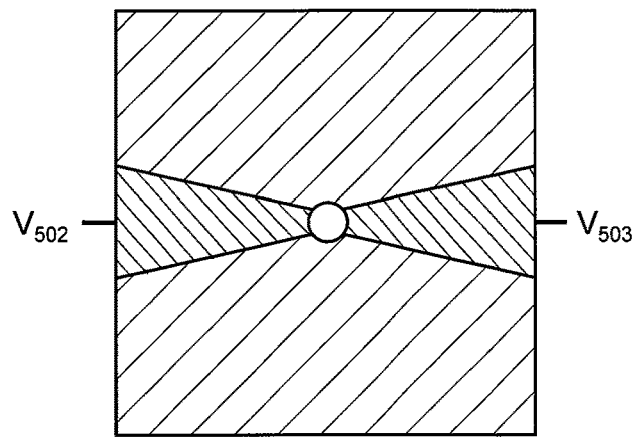

Moreover, FIG. 3-5 shows another embodiment 317 of the substrate.

FIG. 3-5 (a) shows a plane view of the substrate 317. FIG. 3-5 (b) shows a cross-sectional view taken along the line E-E of FIG. 3-5 (c). FIG. 3-5 (c) is a cross-sectional view taken along the line V-V of FIG. 3-5(a).

In the embodiment shown in FIG. 3-5, the nanopore 318 is formed only on the thin membrane 319, and the electrode 320 is provided surrounding the nanopore 318 (namely, around the nanopore). In a procedure of preparing the substrate, the membrane 319 is vapor-deposited on the base 321, the electrode 320 and the insulating layer 322 is formed in advance on the membrane 319 by selective etching or lift-off process using a pattern etc., and thereafter the nanopore 318 is produced in the membrane 319 by an electron beam or an ion beam. Since it is more advantageous in producing the nanopore to make the thickness of the membrane to be processed for a nanopore thinner and the processing of only the thin membrane makes hard it to be contaminated with materials compared to the case where nanopore processing is applied to the thin membrane on which the insulating layer is vapor-deposited, the present embodiment in which the nanopore is provided only in the membrane 319 can realize simple and high quality processing.

Moreover, FIG. 3-6 shows another embodiment 323 of the substrate.

FIG. 3-6 (a) shows a plane view of the substrate 323. FIG. 3-6 (b) shows a cross-sectional view taken along the line F-F of FIG. 3-6 (c). FIG. 3-6 (c) is a cross-sectional view taken along the line VI-VI of FIG. 3-6 (a).

The embodiment shown in FIG. 3-6 is different from the structure of the substrate shown in the embodiment 317 of FIG. 3-5 in the shape of the electrode, and the electrode 324 is formed on the whole surface of the thin membrane except for the part retreated from the nanopore end.

Moreover, FIG. 3-7 shows another embodiment 325 of the substrate.

FIG. 3-7 (a) shows a plane view of the substrate 325. FIG. 3-7 (b) shows a cross-sectional view taken along the line G-G of FIG. 3-7 (c). FIG. 3-7 (c) is a cross-sectional view taken along the line VII-VII of FIG. 3-7 (a).

In the embodiment shown in FIG. 3-7, the sample can be collected from a wider range by disposing electrodes 327 and 328 around the nanopore 326 in a multiple (double) array. For example, in the case where the sample is negatively charged, the sample can be collected near the nanopore 326 by making an electric potential V327 to be applied to the inner electrode 327 and an electric potential V328 to be applied to the outer electrode 328 so as to be V327>V328. In the case where the sample is positively charged, the voltage may be applied in the opposite direction. When the electrodes are made to be a triple or quadruple array, the sample can be collected near the nanopore from a wider range. Furthermore, the sample collected near the nanopore can be transferred through the nanopore in high efficiency by applying voltages so as to be V1<V328≤V327<V2.

Moreover, FIG. 3-8 shows another embodiment 329 of the substrate.

FIG. 3-8 (a) shows a plane view of the substrate 329. FIG. 3-8 (b) shows a cross-sectional view taken along the line H-H of FIG. 3-8 (c). FIG. 3-8 (c) is a cross-sectional view taken along the line VIII-VIII of FIG. 3-8 (a).

The embodiment shown in FIG. 3-8 indicates a technique in which electrodes surround the circumference of the nanopore in a multiple array as with the embodiment of FIG. 3-7, however as shown in the figure, the electrodes can further be made to be multilayered. Electrodes 330 and 331 have a structure in which an electrode member is vapor-deposited on the whole surface (except for the part retreated from the nanopore end) in each layer. In order to collect the sample near the nanopore, for example, in the case where the sample is negatively charged, an electric potential V330 to be applied to the electrode 330 and an electric potential V331 to be applied to the electrode 331 are applied so as to be V330>V331. In the case where the sample is positively charged, the voltage may be applied in the opposite direction. Thereby, the sample can be further strongly collected near the nanopore. Moreover, the disposition of the lead wire to the electrodes becomes easier by making the electrodes multilayered.

In the embodiments shown in FIGS. 3-1 to 3-8, the substrate is shown as the upper part being the thin membrane and the lower part being the base, however when the substrate is disposed in the chamber, the relationship of up-and-down between the thin membrane and the base may be opposite. However, it is preferable that the third electrode is provided on the sample introduction section side.

The biological polymer analyzing equipment with nanopore corresponding to the embodiment of FIG. 3 may be a biological polymer analyzing equipment with nanopore, which has a thin membrane in which one or a plurality of nanometer-sized pores are open; two sections separated by the thin membrane, i.e., a first chamber on the sample introduction side and a second chamber on the sample outflow side; outflow/inflow paths for feeding liquid to the two chamber sections respectively; a first electrode provided in the first chamber and a second electrode provided in the second chamber to apply voltage across the substrate; a third electrode provided near the nanopore; a power source for applying voltage to the electrodes; an amplifier for amplifying an electric signal between electrodes, and an analog-digital converter and a data logger for converting an analog output of the amplifier to a digital output and recording; and in which the third electrode is provided near the first chamber side of both openings of the nanopore.

FIG. 4 shows another embodiment of the present invention.

FIG. 4 (a) shows a nanopore measurement system 401 showing the chamber part of the present invention. FIG. 4 (b) shows a cross-sectional view taken along the line J-J in which the substrate shown in FIG. 4 (a) is cut at the electrode 409 in the direction vertical to the axis of the nanopore 404.

The chamber, the disposition of the nanopore substrate, and the liquid to be used is the same as the embodiment 101 of FIG. 1, however the method for measuring a sample 402 is different in using the tunneling current method instead of the current blockage method. For that purpose, it is preferable that the tunneling current measuring electrodes 405 and 406 facing each other with the nanopore 404 sandwiched therebetween are provided on the nanopore substrate 403. When voltage is applied between the electrode 405 and the electrode 406, a tunneling current flows if the sample 402 is present at a position between the electrodes in the chamber, and it is possible to analyze components of the sample based on the level of the tunneling current. The electrodes 407, 408, and 409 contribute to transferring the sample 402 through the nanopore 404, and in particular the electrode 409 performs a function of collecting the sample 402 near the nanopore 404 as with the electrode 116 in the embodiment 101 of FIG. 1. The sample 402 is transferred through the nanopore 404 with high frequency by collecting the sample 402 near the nanopore 404, which can improve the throughput of the measurement.

The biological polymer analyzing equipment with nanopore corresponding to the embodiment of FIG. 4 may be a biological polymer analyzing equipment with nanopore, which has a thin membrane in which one or a plurality of nanometer-sized pores are open; two sections separated by the thin membrane, i.e., a first chamber on the sample introduction side and a second chamber on the sample outflow side; outflow/inflow paths for feeding liquid to the two chamber sections respectively; a first electrode provided in the first chamber and a second electrode provided in the second chamber to apply voltage across the substrate; a third electrode provided near the nanopore; a fourth electrode and a fifth electrode provided near the third electrode and in the direction orthogonal to the axis of the nanopore, and facing each other; a power source for applying voltage to the electrodes; an amplifier for amplifying an electric signal between electrodes; and an analog-digital converter and a data logger for converting an analog output of the amplifier to a digital output and recording; and in which the third electrode is provided near the first chamber side of the nanopore opening and the fourth and the fifth electrodes are provided near the second chamber side or in the thin membrane in which the nanopore is formed.

FIG. 5 shows another embodiment of the present invention.

FIG. 5 (a) shows a nanopore measurement system 501 showing the chamber part of the present invention. FIG. 5 (b) shows a cross-sectional view taken along the line K-K in which the substrate shown in FIG. 5 (a) is cut at the electrodes 502 and 503 in the direction vertical to the axis of the nanopore.

In the embodiment, the electrodes 502 and 503 that are tunneling current measuring electrodes also perform the function of collecting a sample as a substitute for the electrode 409 of the embodiment of FIG. 4. Analysis of components of the sample 504 is also carried out with a tunneling current generated between electrodes of the electrode 502 and the electrode 503. The transfer of the sample 504 is induced by the electric potential difference between the electrode 505 and the electrode 506. For example, if the sample is negatively charged, force depending on the electric potential difference can be applied to the sample 504 between the electrode 505 and the electrode 502, and between the electrode 505 and the electrode 503 by applying the electric potentials to the electrodes so as to be $V505<V502<V503<V506$ where the electric potentials applied to the electrodes 505, 506, 502, and 503 are expressed as V505, V506, V502, V503, respectively; thereby collecting the sample 504 near the nanopore 507. The collected sample 504 is attracted to the electrode 506, transferred through the nanopore 507, and passes through between the electrode 502 and the electrode 503 during the transfer. Therefore, the component of the sample can be measured by detecting a change in a tunneling current generated between the electrode 502 and the electrode 503.

A step of collecting the sample 504 near the nanopore and a step of detecting the component of the sample 504 may be carried out separately. The voltages may be applied so as to be $V505<V502\leq V503$, and $V506<V502\leq V503$ in the step of collecting the sample 504 and $V505<V502<V503<V506$ in the step of detecting the component of the sample 504.

The biological polymer analyzing equipment with nanopore corresponding to the embodiment of FIG. 5 may be, for example, a biological polymer analyzing equipment with nanopore, which has a thin membrane in which one or a plurality of nanometer-sized pores are open; two sections separated by the thin membrane, i.e., a first chamber on the sample introduction side and a second chamber on the sample outflow side; outflow/inflow paths for feeding liquid to the two chamber sections respectively; a first electrode provided in the first chamber and a second electrode provided in the second chamber to apply voltage across the substrate; a third electrode and a fourth electrode provided near the nanopore and facing each other in the direction orthogonal to the axis of the nanopore; a power source for applying voltage to the electrodes; an amplifier for amplifying an electric signal between electrodes; and an analog-digital converter and a data logger for converting an analog output of the amplifier to a digital output and recording; and in which the third electrode and the fourth electrode are provided near the first chamber side of the nanopore opening.

Figure 6:
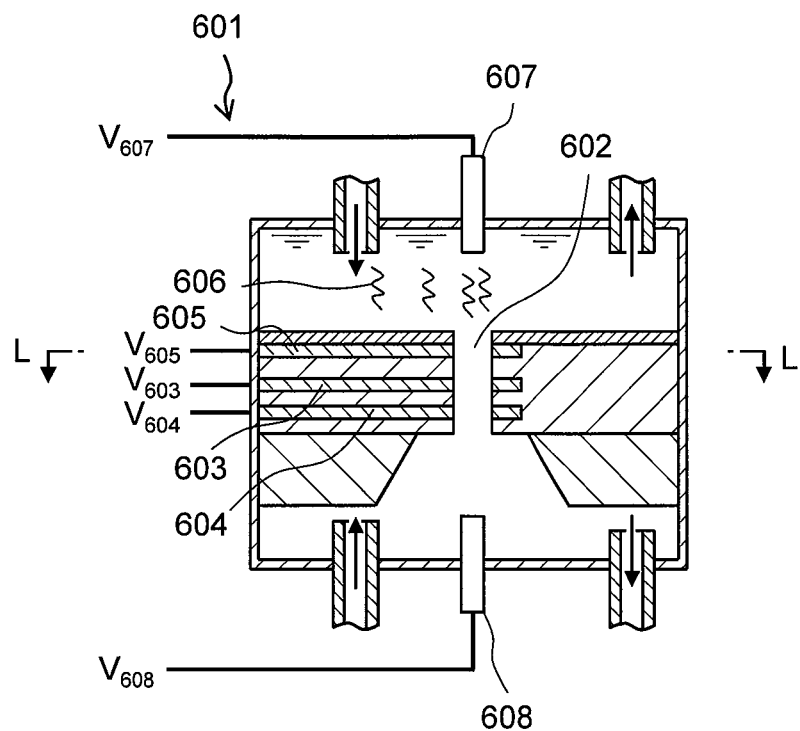
Figure 6:
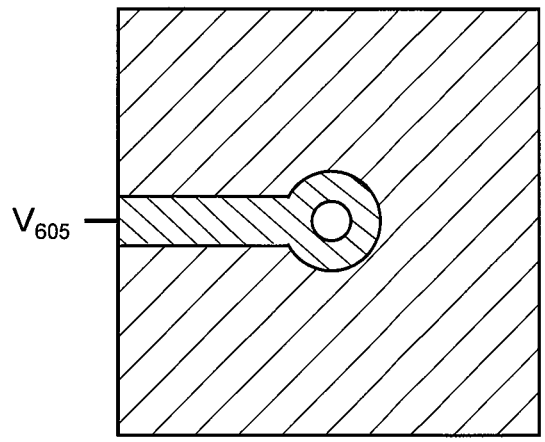

FIG. 6 shows another embodiment of the present invention.

FIG. 6 (a) shows a nanopore measurement system 601 showing the chamber part of the present invention. FIG. 6 (b) shows an cross-sectional view taken along the line L-L in which the substrate shown in FIG. 6 (a) is cut at the electrode 605 in the direction vertical to the axis of the nanopore 602.

In the embodiment, measuring electrodes 603 and 604 are disposed in parallel along the axis direction of the nanopore 602, in place of the tunneling current measuring electrodes 405 and 406 disposed facing each other with the nanopore 404 sandwiched therebetween in the embodiment of FIG. 4. The electrode 605 performs a function of collecting the sample 606 near the nanopore 602, as with the electrode 409 of the embodiment of FIG. 4. It is preferable that the electrodes 603 and 604 are provided extremely close to each other. For example, the distance between the electrode 603 and the electrode 604 is preferably 0.3 nm to 20 nm, more preferably 5 nm or less, further more preferably 2 nm or less. It is also preferable that the electrodes 603 and 604 are separated by an insulating layer. Moreover, the distance between the electrode 605 that is a sample collecting electrode and the measuring electrode 603 is larger than the distance between the electrode 603 and the electrode 604. The distance between the electrode 605 and the measuring electrode 603 is 10 nm or more for example, more preferably 20 nm or more, further more preferably 30 nm or more.

When voltage is applied between the electrode 603 and the electrode 604, a tunneling current according to a component of the sample flows during the sample 606 passing through the nanopore 602. The transfer of the sample is induced by the electric potential differences between the electrodes 607, 608, and 605. For example, if the sample 606 is negatively charged, the sample 606 can be transferred through the nanopore 602 by applying voltages so as to be $V607<V605<V608$ where the voltages to be applied to respective electrodes 607, 608, and 605 are expressed as V607, V608, and V605, respectively. By increasing an electric potential difference between V607 and V605, the sample 606 is collected more near the nanopore 602, the transfer frequency of the sample 606 through the nanopore 602 is increased, and thereby the throughput of the measurement can be improved.

The biological polymer analyzing equipment with nanopore corresponding to the embodiment of FIG. 6 may be, for example, a biological polymer analyzing equipment with nanopore, which has a thin membrane in which one or a plurality of nanometer-sized pores are open; two sections separated by the thin membrane, i.e., a first chamber on the sample introduction side and a second chamber on the sample outflow side; outflow/inflow paths for feeding liquid feeding to the two chamber sections respectively; a first electrode provided in the first chamber and a second electrode provided in the second chamber to apply voltage across the substrate; a third, a fourth, and a fifth electrodes provided near the nanopore; a power source applying voltage to the electrodes; an amplifier for amplifying an electric signal between electrodes; and an analog-digital converter and a data logger for converting an analog output of the amplifier to a digital output and recording; and in which the third electrode is provided near the first chamber side of the nanopore opening, and the fourth and the fifth electrodes are provided near the second chamber side or in the thin membrane in which the nanopore is formed, respective electrodes are disposed in the direction perpendicular to the axis of the nanopore, and the electrodes are disposed in parallel with each other.

Figure 7:
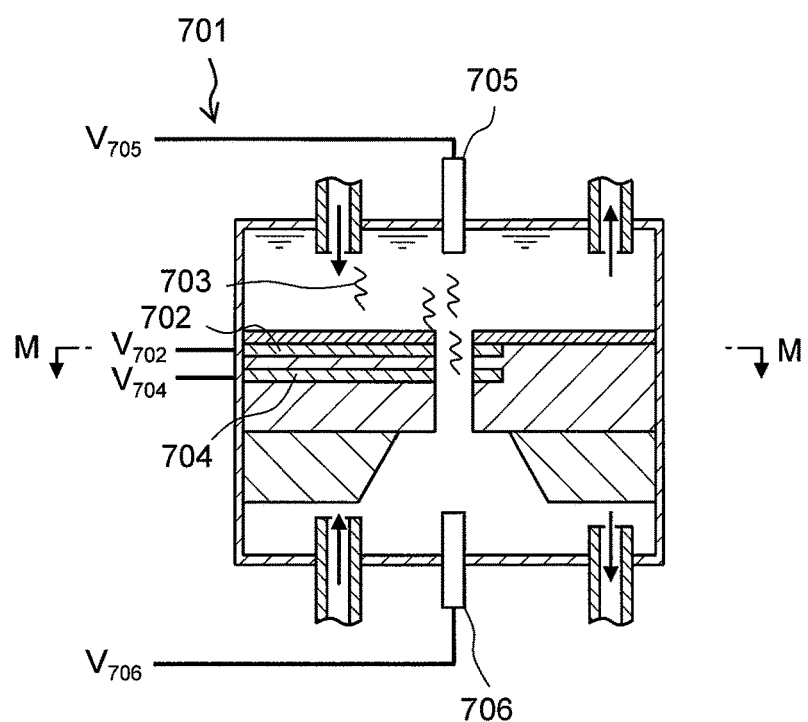
Figure 7:
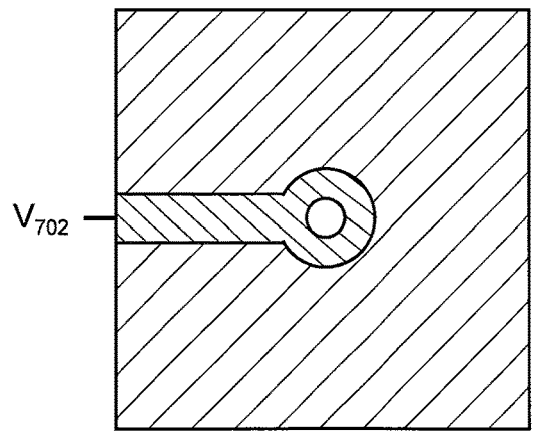

FIG. 7 shows another embodiment of the present invention.

FIG. 7 (a) shows a nanopore measurement system 701 showing the chamber part of the present invention. FIG. 7

(b) shows a cross-sectional view taken along the line M-M in which the substrate shown in FIG. 7 (a) is cut at the electrode 702 in the direction vertical to the axis of the nanopore.

In the embodiment, the electrode 702 that is a tunneling current measuring electrode also performs the function of collecting a sample as a substitute for the electrode 605 of the embodiment of FIG. 6. Analysis of components of the sample 703 is also carried out by utilizing a tunneling current generated between the electrode 702 and the electrode 704. For example, if the sample 703 is negatively charged, by applying voltages so as to be V705<V702<V704<V706 where the voltages to be applied to the electrodes 702, 704, 705, and 706 are expressed as V702, V704, V705, V706, respectively, the sample can be collected between the electrode 705 and the electrode 702 and the components of the sample can be measured by a tunneling current generated between the electrode 702 and the electrode 704.

A step of collecting the sample 703 and a step of detecting the sample 703 may be separated. The voltages may be applied so as to be V705<V702, and V706≤V704≤V702 in the step of collecting the sample 703 and V705<V702<V704<V706 in the step of detecting the sample.

The biological polymer analyzing equipment with nanopore corresponding to the embodiment of FIG. 7 may be, for example, a biological polymer analyzing equipment with nanopore, which has a thin membrane in which one or a plurality of nanometer-sized pores are open; two sections separated by the thin membrane, i.e., a first chamber on the sample introduction side and a second chamber on the sample outflow side; outflow/inflow paths for feeding liquid to the two chamber sections respectively; a first electrode provided in the first chamber and a second electrode provided in the second chamber to apply voltage across the substrate; a third and a fourth electrodes provided near the nanopore; a power source for applying voltage to the electrodes; an amplifier for amplifying an electric signal between electrodes; and an analog-digital converter and a data logger for converting an analog output of the amplifier to a digital output and recording, and in which the third electrode is provided near the first chamber side of the nanopore opening, the fourth electrode is provided near the second chamber side or in the thin membrane in which the nanopore is formed, the respective electrodes are disposed in the direction perpendicular to the axis of the nanopore, electrodes are disposed in parallel with each other, and the distance between the third electrode and the fourth electrode is 5 nm or less, for example 2 nm or less.

FIGS. 4 to 7 show the measurement methods for detecting components in a sample by a tunneling current, however the detecting method may be another method.

Figure 8:
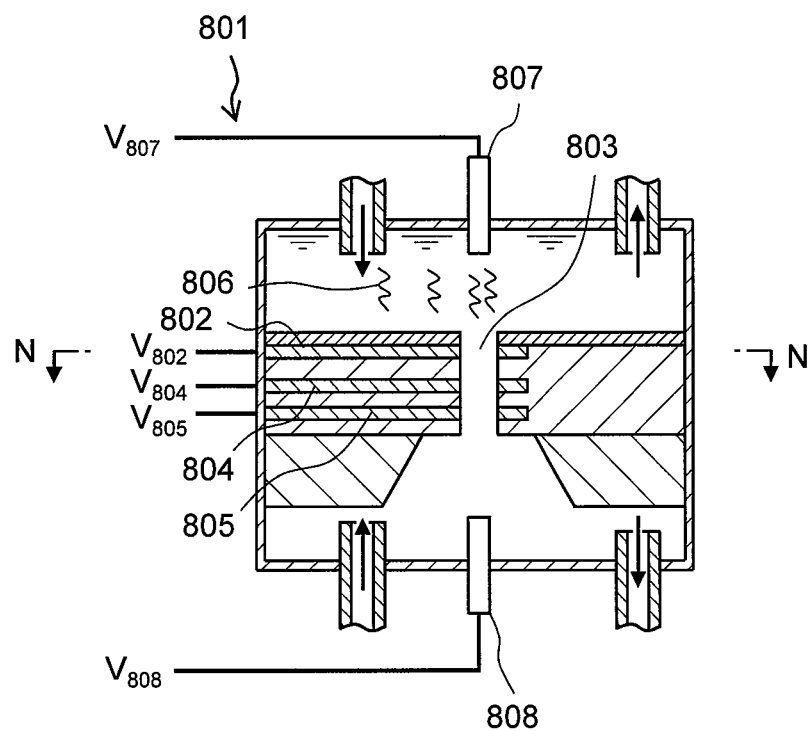
Figure 8:
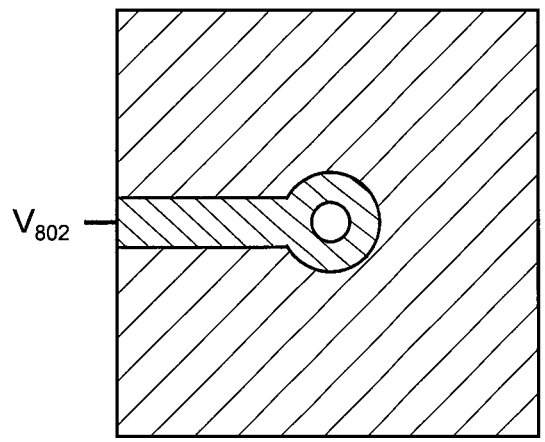

FIG. 8 shows another embodiment of the present invention showing the configuration of the chamber, the nanopore and the electrodes in the case of analyzing components in a sample by capacitance measurement.

FIG. 8 (a) shows a nanopore measurement system 801 showing the chamber part of the present invention. FIG. 8 (b) shows a cross-sectional view taken along the line N-N in which the substrate shown in FIG. 8 (a) is cut at the electrode 802 in the direction vertical to the axis of the nanopore.

In the embodiment, electrodes 802, 804, and 805 are disposed in parallel along the axis direction of the nanopore 803, and the electrode 802 is provided near the nanopore, facing the nanopore 803. The electrode 804 and the electrode 805 are provided at positions in the thin membrane at a position inner relative to the opening of the nanopore 803 closer to the electrode 802, namely at a position closer to the sample outflow section side than the electrode 802.

The distance between the electrode 804 and the electrode 805 is similar to that of the embodiment of FIG. 6 and it is preferable that the electrodes are provided extremely close to each other. For example, the distance between the electrode 804 and the electrode 805 is preferably 0.3 nm to 20 nm, more preferably 5 nm or less, further more preferably 2 nm or less. It is also preferable that the electrodes 804 and 805 are separated by an insulating layer. Moreover, the distance between the electrode 802 that is a sample collecting electrode and the measuring electrode 804 is similar to that of the embodiment of FIG. 6 and is preferably larger than the distance between the electrodes 804 and 805.

In the present embodiment, capacitance can be measured by measuring the voltage between the electrode 804 and the electrode 805 during the sample 806 passing through the nanopore 803, and components of a sample can be analyzed. The electrode 802 performs a function of collecting the sample 806 near the nanopore 803. If the sample is negatively charged, by applying voltages so as to be V807<V802<V808 where the voltages to be applied to respective electrodes 802, 807, and 808 are expressed as V802, V807, and V808, respectively, the sample 806 can be effectively transferred through the nanopore 803.

Figure 9:
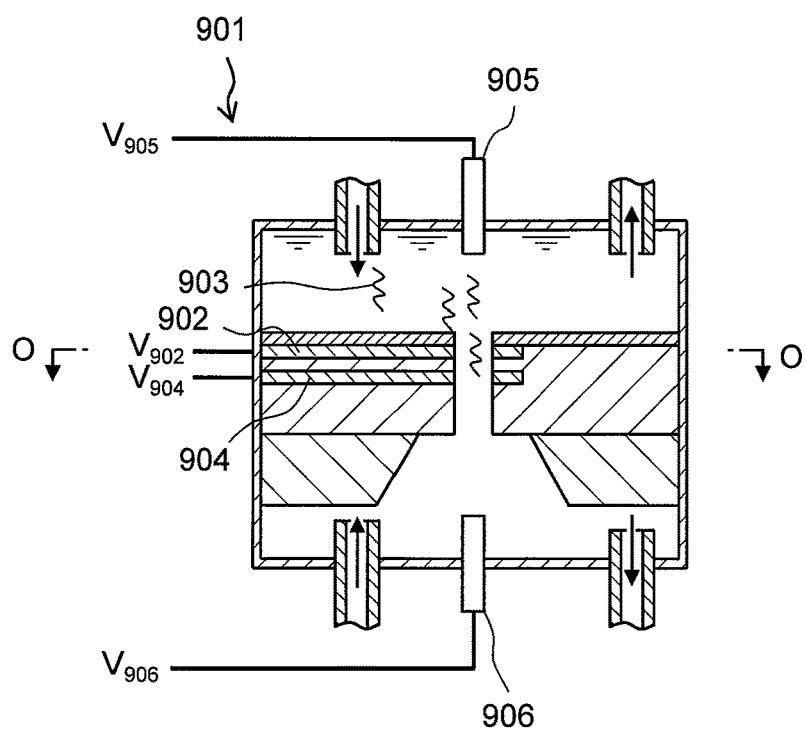
FIG. 9 is a schematic diagram of an analysis chamber part comprising a nanopore substrate on which capacitance measuring electrodes disposed in parallel along an axis direction of a nanopore also work as sample collecting electrodes.
Figure 9:
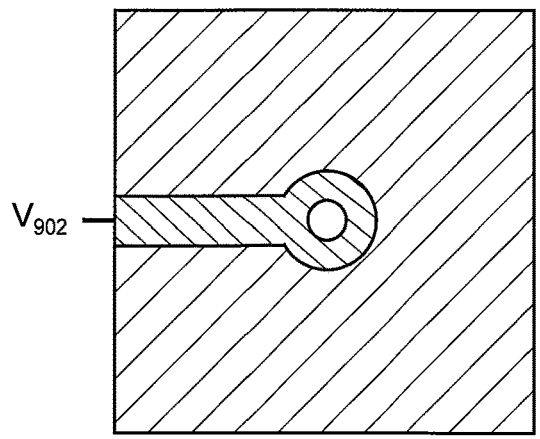

FIG. 9 shows another embodiment of the present invention using capacitance measurement.

FIG. 9 (a) shows a nanopore measurement system 901 showing the chamber part of the present invention. FIG. 9 (b) shows a cross-sectional view taken along the line O-O in which the substrate shown in FIG. 9 (a) is cut at the electrode 902 in the direction vertical to the axis of the nanopore.

In the embodiment, the electrode 902 that is a capacitance measuring electrode also performs the function of collecting a sample as a substitute for the electrode 802 of the embodiment of FIG. 8. Analysis of components in the sample 903 is also carried out by measuring capacitance between the electrode 902 and the electrode 904. For example, if the sample 903 is negatively charged, the sample can be collected between the electrode 905 and the electrode 902 by applying voltages so as to be V905<V902<V906 where the voltages to be applied to the electrodes 902, 904, 905, and 906 are expressed as V902, V904, V905, V906, respectively. And the component of the sample 903 can be measured by measuring capacitance generated between the electrode 902 and the electrode 904.

A step of collecting the sample 903 and a step of detecting the sample 903 may be carried out separately. The voltages may be applied so as to be V905<V902, and V906≤V902 in the step of collecting the sample 903 and V905<V902<V906 in the step of detecting the sample.

Figure 10:
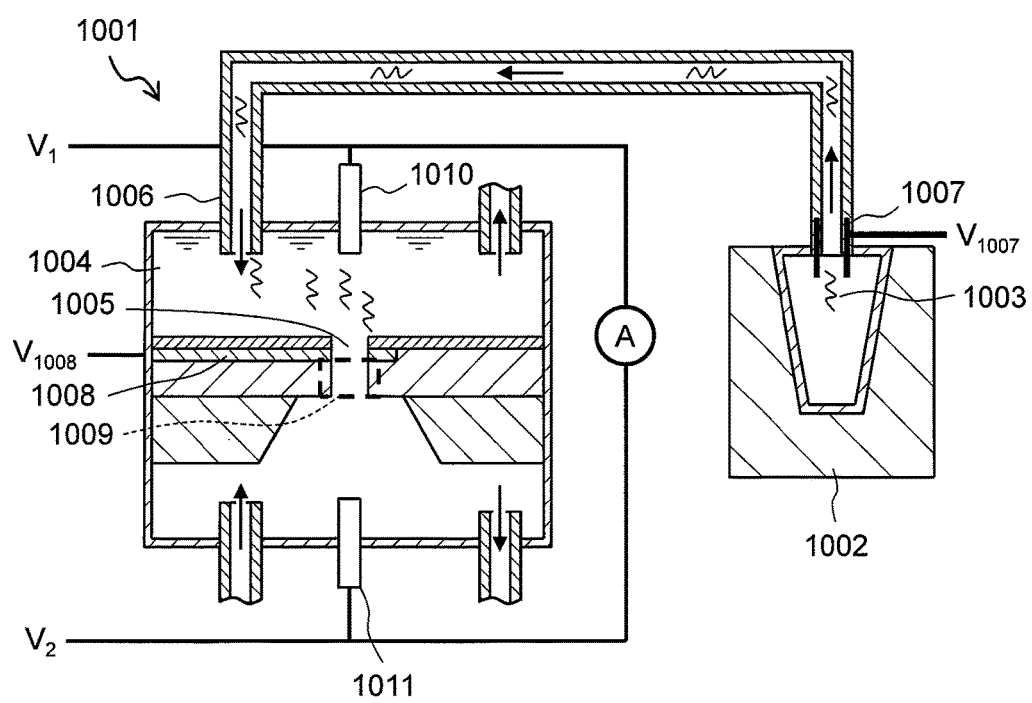
FIG. 10 is a schematic diagram of an analysis chamber part of analyzing equipment with nanopore showing a flow path from a sample container.

FIG. 10 shows an example of embodiments of introducing a sample into the chamber in the present invention. Specifically, a nanopore measurement system 1001 showing the chamber part, the sample container and the flow path of the present invention are shown.

In the embodiment, the sample 1003 is present in the sample container 1002, and the sample 1003 is sucked and delivered into the chamber 1004 and furthermore can be collected near the opening of the nanopore 1005. The electrode 1007 may be provided at the flow path itself or near the flow path on the sample container side of the flow path 1006 connecting the sample container 1002 and the chamber 1004. The sample 1003 is transferred from the sample container 1002 to the opening of the nanopore 1005 via electrophoresis by applying voltage between the electrode 1007 and the electrode 1008 provided at the opening of the nanopore 1005. Coating for preventing or accelerating an electroosmotic flow may be applied to the flow path 1006 according to the state of the charge of the sample 1003.

The detecting part 1009 for the sample 1003 is provided in the region more distant from the opening of the nanopore 1005 than the electrode 1008. Examples of the detection method to be used includes the current blockade method, the tunneling current method, and the capacitance measurement method as described above, and a method of detecting physical, electrical, or chemical changes generated by the interaction of the nanopore and the sample. Moreover, in the case where an electrode is used in the detecting part 1009, the electrode in the detecting part 1009 may also perform the function of transferring the sample 1003 as a substitute for the electrode 1008. In the case, the detecting part 1009 can be provided near the opening of the nanopore 1005 where the sample 1003 is introduced. For example, in the case where the detection is carried out by the current blockade method, voltage is applied between the electrode 1010 and the electrode 1011 and the change in a current value during the sample 1003 passing through the nanopore 1005 is measured. The electrode 1007 performs a function of transferring the sample 1003 from the sample container 1002 to the chamber 1004 and a function of collecting the sample 1003 near the nanopore 1005.

Figures 1, 11:
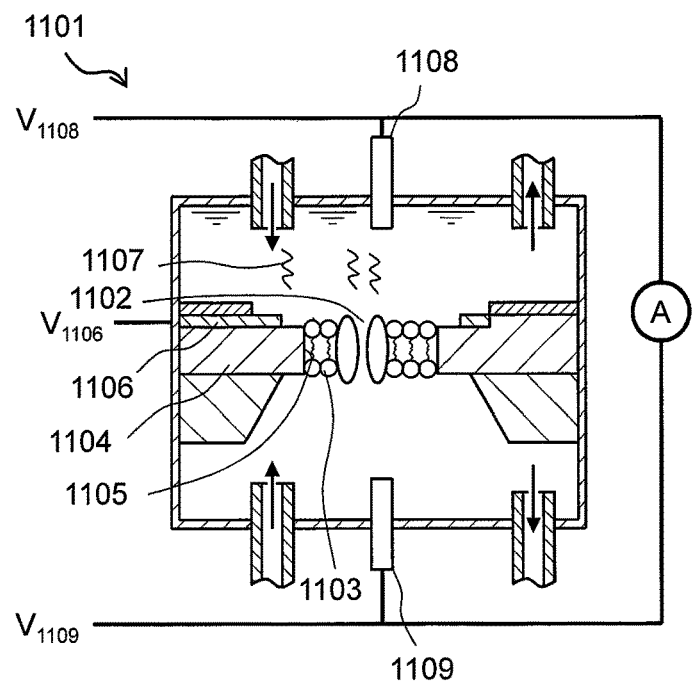
Figures 2, 11:
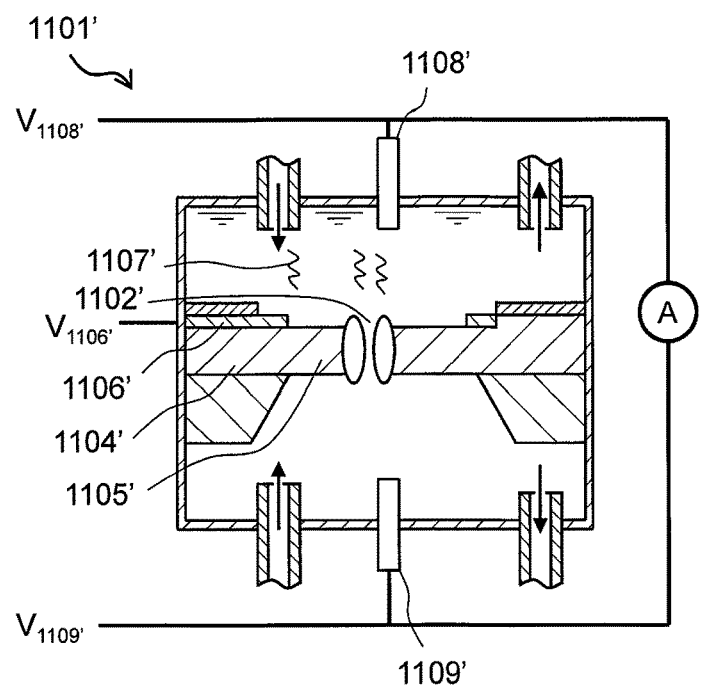

FIG. 11-1 shows a nanopore measurement system 1101 describing an analysis chamber part comprising a nanopore substrate having a sample collecting electrode near a biological nanopore as another embodiment of the present invention.

In the embodiment, a biological nanopore 1102 comprising α-hemolysin etc. is provided in a lipid bilayer membrane 1103, and the lipid bilayer membrane 1103 can be provided in a hole 1105 made in a solid membrane 1104 that can be constituted by a material such as a material made of a resin or silicon compound. Applying voltage to the electrode 1106 provided on the solid membrane 1104 so as to surround the hole 1105 facilitates the collecting of the sample 1107 near the opening of the nanopore 1102.

For example, the current blockade method can be used in a detection method as shown in FIG. 11-1, and in that method, voltages can be applied to the electrode 1108 and the electrode 1109 and the change in a current value between the electrode 1108 and the electrode 1109 during the sample 1107 passing through the biological nanopore 1102 can be measured. If the sample 1107 is negatively charged, the sample can be collected between the electrode 1108 and the electrode 1106 by applying voltages so as to be V1108<V1106<V1109 where the voltages to be applied to respective electrodes 1106, 1108, and 1109 are expressed as V1106, V1108, and V1109, respectively. Furthermore, components of the sample 1107 may be analyzed by measuring a blocked current generated between the electrode 1108 and the electrode 1109.

A step of collecting the sample 1107 and a step of detecting the sample 1107 may be carried out separately. The sample can be effectively transferred through the nanopore by setting the voltages so as to be V1108<V1106, and V1109≤V1106 in the step of collecting the sample 1107 and V1108<V1106<V1109 in the step of detecting the sample 1107.

FIG. 11-2 shows a nanopore measurement system 1101' showing the analysis chamber part comprising a nanopore substrate in which the biological nanopore is directly disposed in the hole in the solid membrane (thin membrane) and a sample collecting electrode is provided near the nanopore, as another embodiment of the present invention. As shown in FIG. 11-2, a nanopore measurement system in which a biological nanopore 1102' is directly disposed in the hole 1105' on the solid membrane 1104' without using a lipid bilayer membrane may be used. The production of the biological nanopore can be carried out as described in, for example, A. R. Hall; A. Scott; D. Rotem; K. L Mehta; H. Bayley; C. Dekker, Nat. Nano., 5, 874 (2010).

Figure 12:
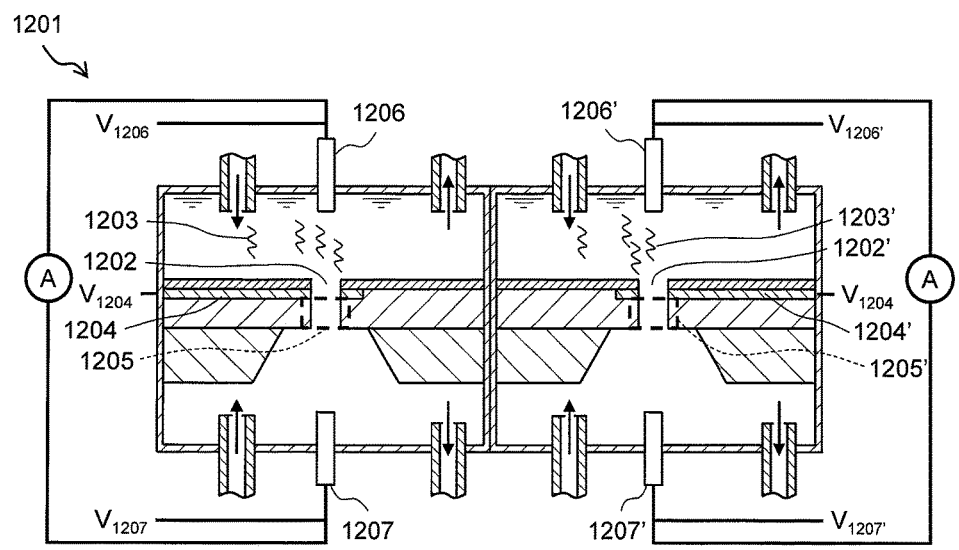
FIG. 12 is a schematic diagram of an analysis chamber part in which a plurality of nanopores and sample collecting electrodes are provided.

FIG. 12 shows another embodiment 1201 of the present invention using an analysis chamber part in which a plurality of nanopores having a sample collecting electrode are provided. The samples 1203 and 1203' can be collected near the respective nanopores 1202 and 1202' by provided electrodes 1204 and 1204', respectively. In the case, the transfer frequencies of the samples 1203, 1203' through respective nanopores 1202 and 1202' can be changed respectively by changing the voltages to be applied to the respective electrodes 1204 and 1204' separately.

It is preferable that the detecting parts 1205 and 1205' directed to the sample 1203 and 1203' are provided at positions more distant from the openings of the nanopores 1202 and 1202' where the sample 1203 and 1203' is introduced and from the electrodes 1204 and 1204', namely at a position closer to the sample outflow section side than the electrodes 1204 and 1204'.

As the detection method for a sample, for example, the current blockade method, the tunneling current method, and the capacitance measurement method may be used, or components of the sample may be detected by a method of detecting physical, electrical, or chemical changes generated by the interaction of the nanopore and the sample. The transfer of the samples 1203 and 1203' through the nanopores 1202 and 1202' is carried out by applying voltages to the electrodes 1206, 1206', 1207, and 1207'. The electrodes 1204 and 1204' may have the same electric potential or may be integrated. In the case, the sample 1203 and 1203' can be collected near the 1202 and 1202' to the same extent respectively.

FIG. 12 shows detecting parts 1205 and 1205' based on the current blockade method. In the case of using the tunneling current method or the capacitance measurement method, the electrodes 1206, 1206', 1207, and 1207' are used only for transferring the sample 1203 and 1203' and do not contribute to the detection. Accordingly, the electrode 1206 and the electrode 1206' may have the same electric potential or may be integrated. Similarly, the electrode 1207 and the electrode 1207' may have the same electric potential or may be integrated.

As shown in FIG. 12, the biological polymer analyzing equipment with nanopore in the present invention may have a plurality of the chamber parts. Two or more chamber parts, for example, 2 to 10 chamber parts may be used. A plurality of chamber parts may be connected so as to be communicated with each other in the chambers.

A plurality of electrodes/flow paths, a plurality of chamber parts, a plurality of nanopores, and a plurality of electrodes mean a structure in which a plurality of respective elements are one-dimensionally or two-dimensionally disposed. Respective elements are shown in the figure, however the number of respective elements in the present embodiment is not limited to two, and the biological polymer analyzing equipment with nanopore may include three, four or more individual elements.

Hereinafter, a method for analyzing a biological polymer using the biological polymer analyzing equipment with nanopore will be described. By using the biological polymer analyzing equipment with nanopore according to the present invention, a sample in a sample solution, in particular, a biological polymer, can be collected highly efficiently near a nanopore and transferred through the nanopore with high frequency. As a result, analysis efficiency of the biological polymer can be greatly increased, and the time for analysis can be shortened.

Specifically, first, a sample solution containing a biological polymer is introduced into the sample introduction section of the biological polymer analyzing equipment with nanopore. Here, the biological polymer may be any polymeric biological molecule. The biological polymer may be a naturally occurring or synthesized one, or may be a derivative or the like that does not exist in nature. The biological polymer can be specifically, for example, but not limited to, nucleic acids such as single strand DNA (ssDNA) and double strand DNA (dsDNA), single strand RNA (ssRNA) and double strand RNA (dsRNA), and hybrid nucleic acids composed of DNA and RNA; peptide nucleic acids; proteins, polypeptides (including peptides of 100-mer or less), for example, proteins, polypeptides and the like composed of D- or L-amino acids; and sugar chains such as sugar chains of polysaccharides and glycoproteins.

The concentration of the sample solution containing a biological polymer is not limited, and good analysis can be carried out even if the concentration is low. For example, the concentration of the sample solution may be 0.1 nM or more, or may be 0.001 nM or more, and it is preferable that the concentration of the sample solution is 0.01 nM to 1000 nM, preferably 0.01 nM to 1 nM.

By making the sample solution containing the biological polymer housed in the sample introduction section and generating an electric potential difference near the opening of the nanopore by using the voltage applying member, a charged biological polymer can be attracted near the opening of the nanopore and corrected it. Subsequently, by generating an electric potential difference between the sample introduction section and the sample outflow section, the biological polymer collected near the opening of the nanopore can be introduced inside the nanopore, transferred through the nanopore so as to be attracted to the sample outflow section.

Applying voltages to respective electrodes may be carried out in the manner as described in the respective embodiments in order to generate the electrical potential difference near the opening of the nanopore by using the voltage applying member.

As an example of the embodiment, for example, in the case of the embodiment of FIG. 1, by making the sample solution containing the biological polymer housed in the sample introduction section and applying voltage between the third electrode and the first electrode, a charged biological polymer can be collected and transferred through the nanopore.

In the case, a negatively charged polymer molecule may be collected by applying voltages to the first, the second, and the third electrodes so that the electric potential of the third electrode is higher than the electric potential of the first electrode and equal to or lower than the electric potential of the second electrode.

Alternatively, a negatively charged biological polymer can be collected and the transfer through the nanopore can be facilitated by applying voltages to the first, the second, and the third electrodes so that the electric potential of the third electrode is higher than the electric potential of the first electrode and equal to or higher than the electric potential of the second electrode and thereafter changing the voltages so that the electric potential of the third electrode becomes lower than the electric potential of the second electrode. Herein, it is preferable that the change of voltage is carried out by a reversible switching element. The reversible switching element is, for example, control device.

Moreover, a positively charged biological polymer may be collected by applying voltages to the first, the second, and the third electrodes so that the electric potential of the third electrode is lower than the electric potential of the first electrode and equal to or higher than the electric potential of the second electrode.

Alternatively, a positively charged polymer molecule can be collected and the transfer through the nanopore can be facilitated by applying voltages to the first, the second, and the third electrodes so that the electric potential of the third electrode is lower than the electric potential of the first electrode and equal to or lower than the electric potential of the second electrode and thereafter changing the voltages so that the electric potential of the third electrode becomes higher than the electric potential of the second electrode.

Furthermore, a biological polymer while passing through the nanopore can be measured by the measuring part of the biological polymer analyzing equipment with nanopore. A conventionally known nanopore-based measurement method may be used for the measurement. For example, a detection method such as the current blockade method, the tunneling current method, or the capacitance measurement method can be used. Alternatively, a detection based on the spectrum of Raman scattering light generated by irradiating external light to the biological polymer may be carried out.

By using the method according to the present invention, a biological polymer can not only be detected but also quantitatively determined, and furthermore the sequence or composition of each monomer constituting the biological polymer can be analyzed, and for example, sequence analysis or the like can be carried out. The method and the analyzing equipment of the present invention are suitable for analysis of a biological polymer having a comparatively large size that has been difficult to analyze so far. The method and the analyzing equipment of the present invention is of course capable of, in the case of a DNA for example, analyzing a DNA having a length as short as less than 1 kb well, however the method and the analyzing equipment of the present invention are particularly suitable for analyzing a DNA having a length of preferably 1 kb or more, more preferably 3 kb or more, particularly preferable 4 kb or more, and for example 1 to 5 kb or more, via transferring it through the nanopore. Furthermore, the method of the present invention is suitable for analyzing a biological polymer having a low concentration in a sample solution.

Those skilled in the art would easily recognize that the present invention is not limited to the above-described embodiments and various changes are possible within the scope of the claimed invention.

All the publications, patents, and patent applications cited in the present description are incorporated into the present description by reference in their entirety.

REFERENCE SIGNS LIST

101 Chamber
102 Nanopore
103 Nanopore substrate
104 Space (Sample introduction section)
105 Space (Sample outflow section)

106 Inflow path
107 Inflow path
108 Outflow path
109 Outflow path
110 Liquid
111 Liquid
112 Electrolyte liquid
113 Sample
114 Electrode
115 Electrode
116 Electrode
117 Ammeter
201 Chamber
202 Nanopore
203 Nanopore substrate
204 Space (Sample introduction section)
205 Space (Sample outflow section)
206 Inflow path
207 Inflow path
208 Outflow path
209 Outflow path
210 Liquid
211 Liquid
212 Sample
213 Electrode
214 Electrode
215 Ammeter
301 Substrate
302 Base
303 Membrane
304 Electrode
305 Insulating layer
306 Nanopore
307 Substrate
308 Electrode
309 Substrate
310 Electrode
311 Space
312 Insulating layer
313 Substrate
314 Electrode
315 Space
316 Insulating layer
317 Substrate
318 Nanopore
319 Membrane
320 Electrode
321 Base
322 Insulating layer
323 Substrate
324 Electrode
325 Substrate
326 Nanopore
327 Electrode
328 Electrode
329 Substrate
330 Electrode
331 Electrode
401 Nanopore measurement system
402 Sample
403 Nanopore substrate
404 Nanopore
405 Tunneling current measuring electrode
406 Tunneling current measuring electrode
407 Electrode
408 Electrode
409 Electrode
501 Nanopore measurement system
502 Electrode
503 Electrode
504 Sample
505 Electrode
506 Electrode
507 Nanopore
601 Nanopore measurement system
602 Nanopore
603 Tunneling current measuring electrode
604 Tunneling current measuring electrode
605 Electrode
606 Sample
607 Electrode
608 Electrode
701 Nanopore measurement system
702 Electrode
703 Sample
704 Electrode
705 Electrode
801 Nanopore measurement system
802 Electrode
803 Nanopore
804 Electrode
805 Electrode
806 Sample
807 Electrode
808 Electrode
901 Nanopore measurement system
902 Electrode
903 Sample
904 Electrode
905 Electrode
906 Electrode
1001 Nanopore measurement system
1002 Sample container
1003 Sample
1004 Chamber
1005 Nanopore
1006 Flow path
1007 Electrode
1008 Electrode
1009 Detecting part
1010 Electrode
1011 Electrode
1101 Nanopore measurement system
1102 Biological nanopore
1103 Lipid bilayer membrane
1104 Solid membrane
1105 Hole
1106 Electrode
1107 Sample
1108 Electrode
1109 Electrode
1201 Nanopore measurement system
1202 Nanopore
1202' Nanopore
1203 Sample
1203' Sample
1204 Electrode
1204' Electrode
1205 Detecting part
1205' Detecting part
1206 Electrode
1206' Electrode
1207 Electrode
1207' Electrode

The invention claimed is:

1. A biological polymer analyzing apparatus to measure tunneling current comprising:
a chamber having a sample introduction section and a sample outflow section separated by a substrate;
a first electrode disposed in the sample introduction section;
a second electrode disposed in the sample outflow section;
a membrane disposed on the substrate;
a nanopore disposed in the membrane of the substrate to communicate between the sample introduction section and the sample outflow section;
a third electrode disposed over the membrane and which completely surrounds a circumference of the nanopore;
an insulating layer disposed on the third electrode and facing a side of the sample introduction section and which defines a space which exposes an upper surface of the third electrode around the nanopore to the sample introduction section; and
a pair of tunneling current measuring electrodes disposed on sides of the nanopore between the third electrode and the substrate; and
wherein the pair of tunneling current measuring electrodes are disposed facing each other with the nanopore sandwiched therebetween,
wherein the third electrode is separated from the first electrode and the second electrode, and
wherein the third electrode is separated from the pair of tunneling current measuring electrodes.

2. The biological polymer analyzing apparatus according to claim 1, further comprising:
an ammeter configured to measure a current between the pair of tunneling current measuring electrodes.

3. The biological polymer analyzing apparatus according to claim 2, wherein the pair of tunneling current measuring electrodes are provided near an opening of the nanopore or in the membrane.

4. The biological polymer analyzing apparatus according to claim 1, wherein the nanopore has a diameter of 1 nm to 100 nm at the minimum diameter part.

5. The biological polymer analyzing apparatus according to claim 1, wherein a voltage applied between the third electrode and the second electrode is switched between plural values.

6. The biological polymer analyzing apparatus according to claim 1, wherein the third electrode is disposed to completely surround the circumference of the nanopore on a side of the sample introduction section,
wherein the exposed upper surface of the third electrode includes a plurality of concentric rings, and
wherein the space which exposes the upper surface of the third electrode is larger than an opening of the nanopore in a plan view.

7. The biological polymer analyzing apparatus according to claim 1, wherein the third electrode covers a whole surface of the membrane except for an opening of the nanopore.

8. The biological polymer analyzing apparatus according to claim 1, wherein the third electrode comprises two or more electrodes disposed in a multiple array and/or a multilayer, and
wherein the two or more electrodes of the third electrode are disposed at positions facing each other with the nanopore therebetween.

9. A biological polymer analyzing apparatus to measure tunneling current comprising:
a plurality of chambers, where each of the chambers respectively includes:
a substrate separating the respective chamber into a sample introduction section and a sample outflow section;
a first electrode disposed in the sample introduction section;
a second electrode disposed in the sample outflow section;
a membrane disposed on the substrate;
a nanopore disposed in the membrane of the substrate to communicate between the sample introduction section and the sample outflow section;
a third electrode disposed over the membrane and which completely surrounds a circumference of the nanopore;
an insulating layer disposed on the third electrode and facing a side of the sample introduction section and which defines a space which exposes an upper surface of the third electrode around the nanopore to the sample introduction section;
a pair of tunneling current measuring electrodes disposed on sides of the nanopore between the third electrode and the substrate;
wherein the pair of tunneling current measuring electrodes are disposed facing each other with the nanopore sandwiched therebetween,
wherein the third electrode is separated from the first electrode and the second electrode in the respective chamber, and
wherein the third electrode is separated from the pair of tunneling current measuring electrodes.

10. The biological polymer analyzing apparatus according to claim 9, further comprising:
an ammeter configured to measure a current between the pair of tunneling current measuring electrodes.

11. The biological polymer analyzing apparatus according to claim 9, wherein the nanopore has a diameter of 1 nm to 100 nm at the minimum diameter part.

12. The biological polymer analyzing apparatus according to claim 9, wherein a voltage applied between the third electrode and the second electrode is switched between plural values.

13. The biological polymer analyzing apparatus according to claim 9, wherein the third electrode is disposed to completely surround the circumference of the nanopore on a side of the sample introduction section,
wherein the exposed upper surface of the third electrode includes a plurality of concentric rings, and
wherein the space which exposes the upper surface of the third electrode is larger than an opening of the nanopore in a plan view.

14. The biological polymer analyzing apparatus according to claim 9, wherein the third electrode covers a whole surface of the membrane except for an opening of the nanopore, and
wherein the space which exposes the upper surface of the third electrode is larger than the opening of the nanopore in a plan view.

* * * * *